（12）United States Patent
Manivannan et al.

(10) Patent No.: US 12,165,434 B2
(45) Date of Patent: Dec. 10, 2024

(54) SEGMENTATION AND CLASSIFICATION OF GEOGRAPHIC ATROPHY PATTERNS IN PATIENTS WITH AGE RELATED MACULAR DEGENERATION IN WIDEFIELD AUTOFLUORESCENCE IMAGES

(71) Applicants: Carl Zeiss Meditec, Inc., Dublin, CA (US); Carl Zeiss Meditec AG, Jena (DE)

(72) Inventors: Niranchana Manivannan, Fremont, CA (US); Mary Durbin, San Francisco, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 437 days.

(21) Appl. No.: 17/426,247

(22) PCT Filed: Feb. 6, 2020

(86) PCT No.: PCT/EP2020/000037
§ 371 (c)(1),
(2) Date: Jul. 28, 2021

(87) PCT Pub. No.: WO2020/160839
PCT Pub. Date: Aug. 13, 2020

(65) Prior Publication Data
US 2022/0084210 A1  Mar. 17, 2022

Related U.S. Application Data

(60) Provisional application No. 62/802,728, filed on Feb. 8, 2019.

(51) Int. Cl.
*G06V 40/18* (2022.01)
*A61B 3/12* (2006.01)
(Continued)

(52) U.S. Cl.
CPC .............. *G06V 40/197* (2022.01); *A61B 3/12* (2013.01); *G06T 7/149* (2017.01); *G06V 10/421* (2022.01);
(Continued)

(58) Field of Classification Search
None
See application file for complete search history.

(56) References Cited

U.S. PATENT DOCUMENTS 6,549,801 B1   4/2003   Chen et al.
6,741,359 B2   5/2004   Wei et al.
(Continued)

FOREIGN PATENT DOCUMENTS

| JP | 2016131881 | 7/2016 |
|---|---|---|
| WO | WO-2012059236 A1 | 5/2012 |
| WO | WO-2016124644 A1 | 8/2016 |

OTHER PUBLICATIONS

Abràmoff et al., (2010). "Retinal Imaging and Image Analysis", IEEE Reviews in Biomedical Engineering, 3:169-208.
(Continued)

*Primary Examiner* — Leon Flores
(74) *Attorney, Agent, or Firm* — Snell & Wilmer L.L.P.

(57) ABSTRACT

An automated segmentation and identification system/method for identifying geographic atrophy (GA) phenotypic patterns in fundus autofluorescence images. A hybrid process combines a supervised pixel classifier with an active contour algorithm. A trained, machine learning model (e.g., SVM or U-Net) provides initial GA segmentation/classification, and this is followed by Chan-Vese active contour algorithm. The junctional zones of the GA segmented area are then analyzed for geometric regularity and light intensity regularity. A determination of GA phenotype is made, at least in part, from these parameters.

16 Claims, 14 Drawing Sheets

(51) Int. Cl.
*G06T 7/149* (2017.01)
*G06V 10/42* (2022.01)
*G06V 10/46* (2022.01)
*G06V 10/82* (2022.01)
*G06V 10/25* (2022.01)

(52) U.S. Cl.
CPC ............ *G06V 10/469* (2022.01); *G06V 10/82* (2022.01); *G06V 40/193* (2022.01); *G06T 2207/20081* (2013.01); *G06T 2207/20084* (2013.01); *G06T 2207/20104* (2013.01); *G06T 2207/30041* (2013.01); *G06V 10/25* (2022.01)

(56) References Cited

U.S. PATENT DOCUMENTS

| | | |
|---|---|---|
| 7,301,644 B2 | 11/2007 | Knighton et al. |
| 8,967,806 B2 | 3/2015 | Bublitz et al. |
| 8,998,411 B2 | 4/2015 | Tumlinson et al. |
| 9,332,902 B2 | 5/2016 | Tumlinson et al. |
| 9,456,746 B2 | 10/2016 | Bublitz et al. |
| 9,700,206 B2 | 7/2017 | An et al. |
| 9,706,915 B2 | 7/2017 | Everett et al. |
| 9,759,544 B2 | 9/2017 | An et al. |
| 2005/0171438 A1 | 8/2005 | Chen et al. |
| 2010/0027857 A1 | 2/2010 | Wang |
| 2012/0277579 A1 | 11/2012 | Sharma et al. |
| 2012/0307014 A1 | 12/2012 | Wang |
| 2015/0131050 A1 | 5/2015 | Bublitz et al. |
| 2016/0206190 A1 | 7/2016 | Reisman et al. |
| 2016/0345819 A1 | 12/2016 | Jayasundera et al. |
| 2019/0005684 A1 | 1/2019 | De Fauw et al. |

OTHER PUBLICATIONS

Bindewald et al., (2005). "Classification of fundus autofluorescence patterns in early age-related macular disease," Invest Ophthalmol Vis Sci., 46:3309-3314.

Blazkiewicz et al., (2005). "Signal-to-noise ratio study of full-field Fourier-domain optical coherence tomography," Applied Optics, 44(36):7722-7729.

Chen et al., (2013). "Semi-automatic geographic atrophy segmentation for SD-OCT images," Biomedical Optics Express, 4(12):2729-2750.

Cheriyan et al., (2012). "3D Reconstruction of Human Retina from Fundus Image—A Survey", International Journal of Modern Engineering Research, 2(5):3089-3092.

Fleckenstein et al., (2014). "The "Diffuse-Trickling" Fundus Autofluorescence in phenotype in geographic atrophy," Invest Ophthalmol Vis Sci., 55:2911-2920.

Hillmann et al., (2011). "Holoscopy—holographic optical coherence tomography," Optics Letters, 36(13):2390-2392.

Holz et al., (2007). "Progression of geographic atrophy and impact of fundus autofluorescence patterns in age-related macular degeneration," Am J Ophthalmol, 143:463-472.

Hu et al., (2013). "Segmentation of the geographic atrophy in spectral-domain optical coherence tomography and fundus autofluorescence images," Invest Ophthalmol Vis Sci., 54:8375-8383.

Hu et al., (2015). "Automated segmentation of geographic atrophy in fundus autofluorescence images using supervised pixel classification." J. of Medical Imaging, 2(1):014501, 7 pages.

International Search Report and Written Opinion received for International Patent Application No. PCT/EP2020/000037 mailed on Jul. 20, 2020, 17 pages.

Jeong et al., (2014). "Predictors for the progression of geographic atrophy in patients with age-related macular degeneration: fundus autofluorescence study with modified fundus camera." Eye, 28(2):209-218, 10 pages.

Lee et al., (2008). "Interactive segmentation for geographic atrophy in retinal fundus images," 2008 42nd Asilomar Conference on Signals, Systems and Computers, 1399:1-4.

Nakamura et al., (2007). "High-Speed three dimensional human retinal imaging by line field spectral domain optical coherence tomography," Optics Express, 15(12):7103-7116.

Niu et al., (2016). "Automated geographic atrophy segmentation for SD-OCT images using region-based C-V model via local similarity factor," Biomedical Optics Express, 7(2), 581-600.

Schmitz-Valckenberg et al., (2011). "Semiautomated image processing method for identification and quantification of geographic atrophy in age-related macular degeneration," Invest Ophthalmol Vis Sci., 52:7640-7646.

Treder et al., (2018). "Deep learning-based detection and classification of geographic atrophy using a deep convolutional neural network classifier," Graefe's Archive for Clinical and Experimental Ophthalmology, 256(11):2053-2060.

Japan Patent Office; Japan Office Action dated Feb. 6, 2024 in Application No. 2021-538343.

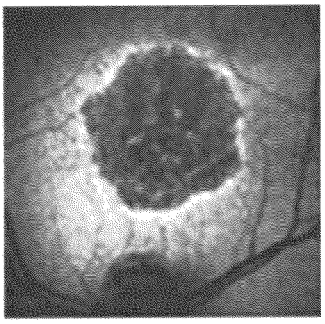
FIG. 2 Geographic Atrophy
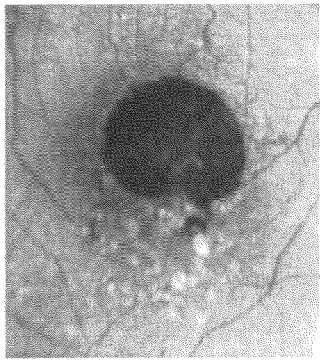
FIG. 3B Banded GA
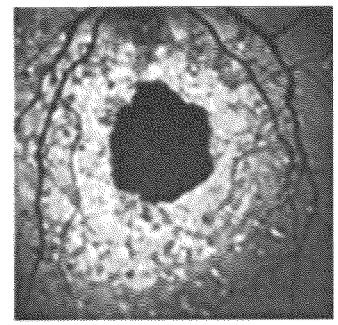
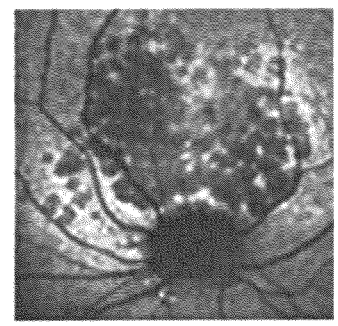
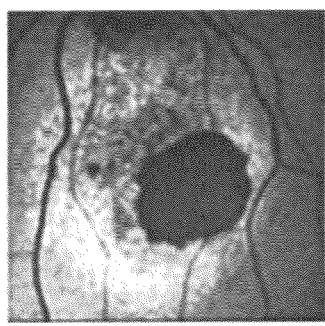
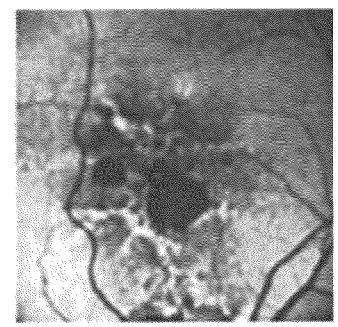
FIG. 3A Diffused GA

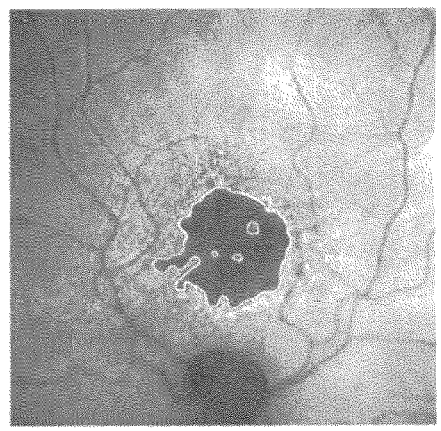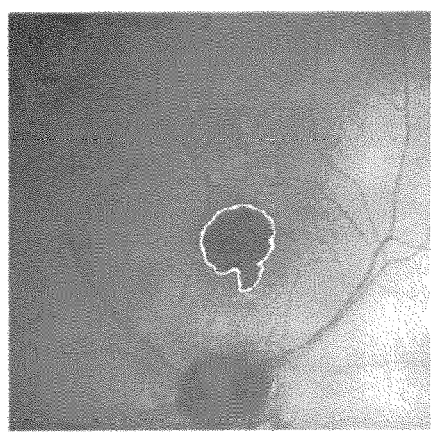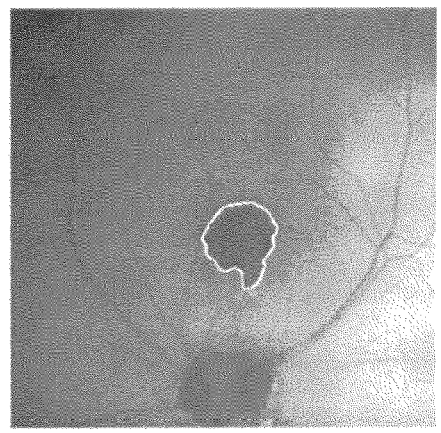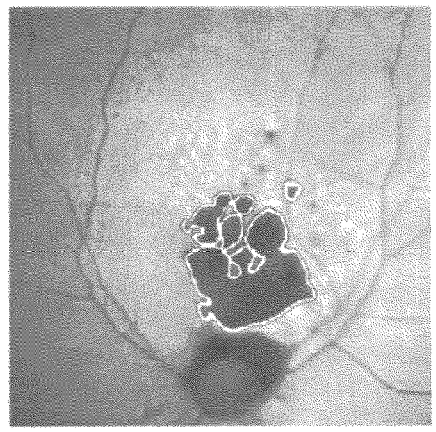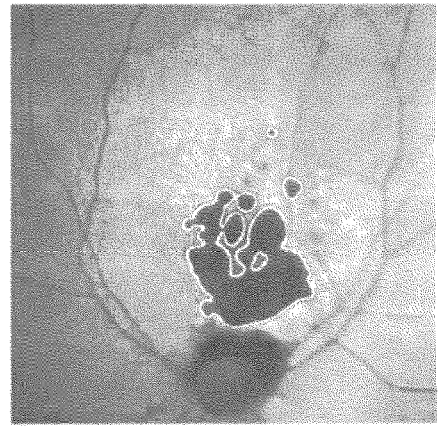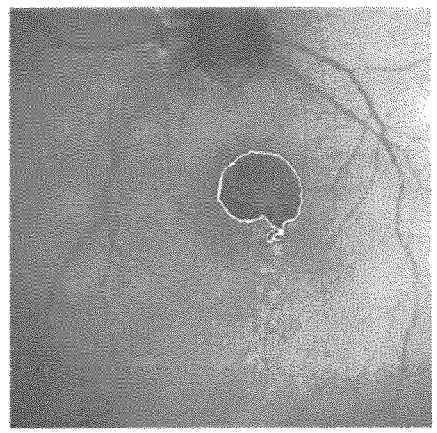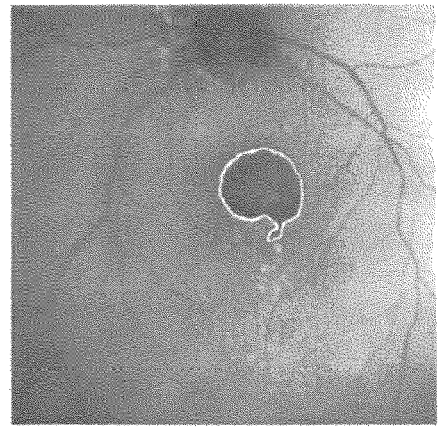
FIG. 6
FIG. 7

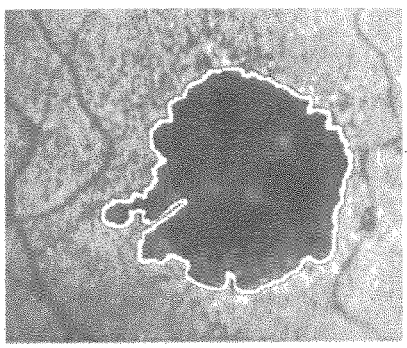
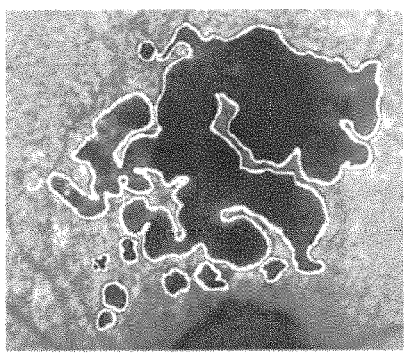
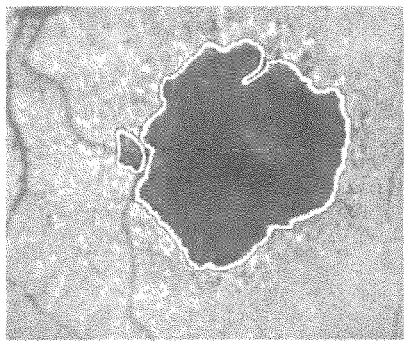
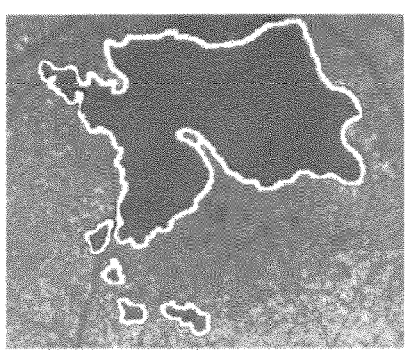
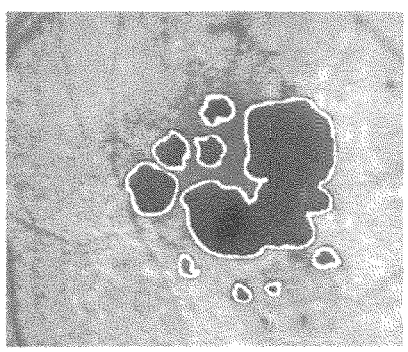
FIG. 8
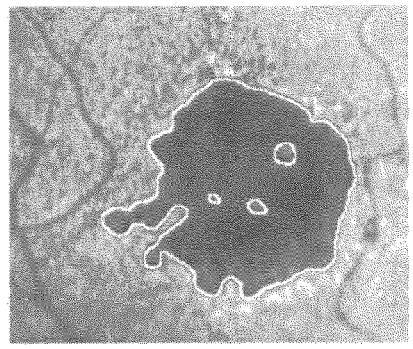
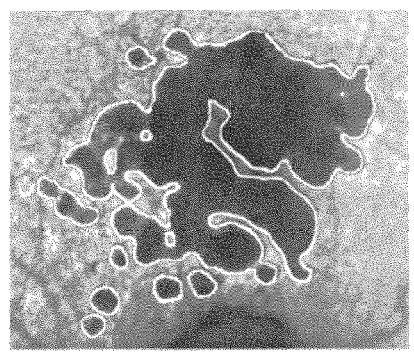
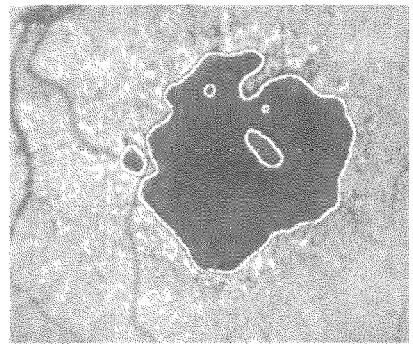
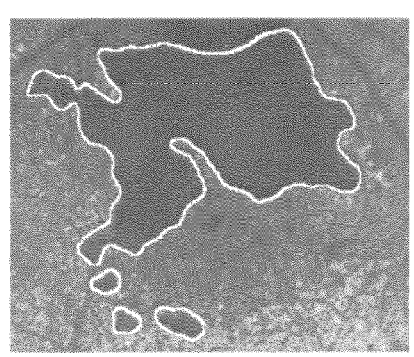
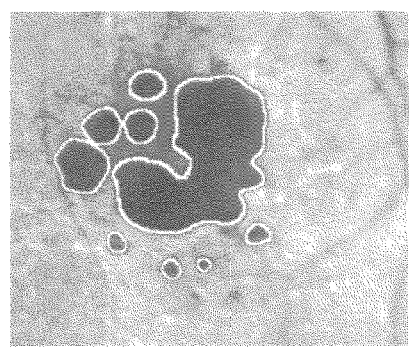
FIG. 9

SEGMENTATION AND CLASSIFICATION OF GEOGRAPHIC ATROPHY PATTERNS IN PATIENTS WITH AGE RELATED MACULAR DEGENERATION IN WIDEFIELD AUTOFLUORESCENCE IMAGES

PRIORITY

This application is a National Phase application under 35 U.S.C. § 371 of International Application No. PCT/EP2020/000037, filed Feb. 6, 2020, which claims priority to U.S. Provisional Application Ser. No. 62/802,728, filed Feb. 8, 2019, the contents of which are hereby incorporated by reference in their entirety.

FIELD OF INVENTION

The present invention is generally directed to the field of ophthalmic autofluorescence images. More specifically, it is directed toward the classification of geographic atrophy regions found in fundus autofluorescence images.

BACKGROUND

Age-related macular degeneration (AMD) is the most frequent cause of blindness in older population in industrialized countries. Geographic atrophy (GA) is an advanced form of AMD characterized by loss of photoreceptors, retinal pigment epithelium (RPE), and choriocapillaris. Five million people are estimated to be affected by geographic atrophy globally. GA can result in irreversible visual functional loss and is responsible for approximately 20% of the severe vision impairment from AMD. There are no approved treatments to date to counteract the progression of GA. In recent years, however, progress in understanding the pathogenesis of GA has led to several potential therapies in clinical trials. Nonetheless, early identification of GA progression is vital to slowing its effects.

Different phenotypic patterns of abnormal fundus autofluorescence (FAF) images have been shown to be helpful in identifying GA progression. Identification of GA lesions and their phenotypes can therefore be important factors in determining disease progression and clinical diagnosis of AMD. Use of medical personnel to visually inspect FAF images for GA lesions and their phenotypes is effective, but time consuming. A few segmentation algorithms have been developed to aid in assessing GA lesions, but many of these algorithms are semi-automated and require manual input for segmentation of GA lesions.

It is an object of the present invention to provide a fully automated method for quantification of GA lesions and their phenotype patterns in medical images.

It is another object of the present invention to augment GA lesion segmentation algorithms with the ability to identify and classify different phenotypic patterns.

It is a further object of the present invention to provide a framework for automated segmentation and identification of GA phenotypic patterns in widefield FAF images.

SUMMARY OF INVENTION

The above objects are met in a system/method for classifying (e.g., identifying) geographic atrophy (GA) in an eye. For example, a GA region (e.g., GA segmentation in a fundus or en face image) may be identified as 'diffused' phenotype or 'banded' phenotype. Both of these phenotypes have been empirically determined to be indicative of high progression rate geographic atrophy. The system may include an ophthalmic diagnostic device, such as a fundus imager or optical coherence tomography (OCT) device used to generate/capture an ophthalmic image. Alternatively, the ophthalmic diagnostic device may embody a computer system that accesses a pre-existing ophthalmic image from a data store using a computer network, e.g., the Internet. The ophthalmic diagnostic device is used to acquire an image of the fundus of the eye. Preferably, the image is a fundus autofluorescence (FAF) image since GA lesions are typically more easily discernable in such images.

The acquired image is then submitted to an automated GA identification process to identify (e.g., segment) a GA region in the image. The present GA segmentation process is fully automated, and may be based on a deep learning neural network. GA segmentation may further be based on a two-stage segmentation process, e.g., a hybrid process that combines a supervised classifier (or pixel/image-segment segmentation) with an active contour algorithm. The supervised classifier is preferably a machine learning (ML) model, and may be implemented as a support vector machine (SVM) or a deep learning neural network, preferably a U-Net type convolutional neural network. This first stage classifier/segmentation ML model identifies initial GA regions (lesions) in the image, and the results are fed to the active counter algorithm for a second stage segmentation. The active contour algorithm may be implemented as a modified Chase-Vese segmentation algorithm, where the initial GA regions identified in the first stage are used as starting points (e.g., initial contours) in the Chase-Vese segmentation. The result is a robust GA segmentation of the acquired image.

The identified GA regions are then submitted for analysis to identify their specific phenotype. For example, the system/method may use a contour-non-uniformity measure of the GA region(s) to identify a 'diffused' phenotype, and use an intensity-uniformity measure to identify a 'banded' phenotype. Either of these two phenotypes indicates a high progression rate GA region. This analysis may be made in a two-step process, where a first of two measures is calculated, and if the first measure is higher than a first threshold, then the GA region may be classified as high-progression-rate, and there is no need to calculate the second of the two measurements. However, if the first measure is not higher than the first threshold, then the second measure may be calculated and compared with a second threshold to determine if it indicates high-progression-rate GA. For example, if the contour-non-uniformity measure is greater than a first predefined threshold (e.g., the non-uniformity of the perimeter contour of the GA region is greater than the predefined threshold), then the GA region may be classified as 'diffused' phenotype, and if the intensity-uniformity measure is greater than a second threshold, then the GA region may be classified as 'banded' phenotype.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 2 provides an example FAF image of a GA region.

FIG. 3A provides some FAF image examples of GA lesions of 'diffused' phenotype.

FIG. 3B provides an FAF example of a GA lesion of 'banded' phenotype.

FIG. 6 shows four GA regions delineated by human experts.

FIG. 7 shows GA delineation provided by a support vector machine and corresponding to the GA regions of FIG. 6.

FIG. 8 shows five GA regions delineated by human experts.

FIG. 9 shows GA delineation provided by a deep learning, neural network and corresponding to GA regions of FIG. 8.

DESCRIPTION OF THE PREFERRED EMBODIMENTS

Early diagnosis is critical for the successful treatment of various eye diseases. Optical imaging is a preferred method for non-invasive examination of the retina. Although age-related macular degeneration (AMD) is known to be a major causes of vision loss, diagnosis is often not made until after damage has manifested itself. Therefore, a goal of advanced ophthalmic imaging devices is to provide diagnostic tools to help detect and monitor pathological variations at a pre-clinical stage of disease.

Multiple ophthalmic imaging systems are known the art, such as fundus imaging systems and optical coherence tomography systems, any which may be used with the present invention. Examples of ophthalmic imaging modalities are provided below, see for example, FIGS. 13 and 14. Any of these devices may be used to provide an image of the fundus of an eye, which is the interior surface of the eye opposite the eye lens (or crystalline lens) and may include the retina, optic disc, macula, fovea, and posterior pole.

Ophthalmic imaging systems may generate full color images. Other imaging techniques, such as fluorescein angiography or indocyanine green angiography (ICG), may be used to capture high contrast images of specific ophthalmic features, such as blood vessels or lesions. High contrast images are obtained by collecting images after a fluorescent dye is injected into a subject's bloodstream and capturing the images using specific light frequencies (e.g., colors) selected to excite the fluorescent dye.

Figure 1:
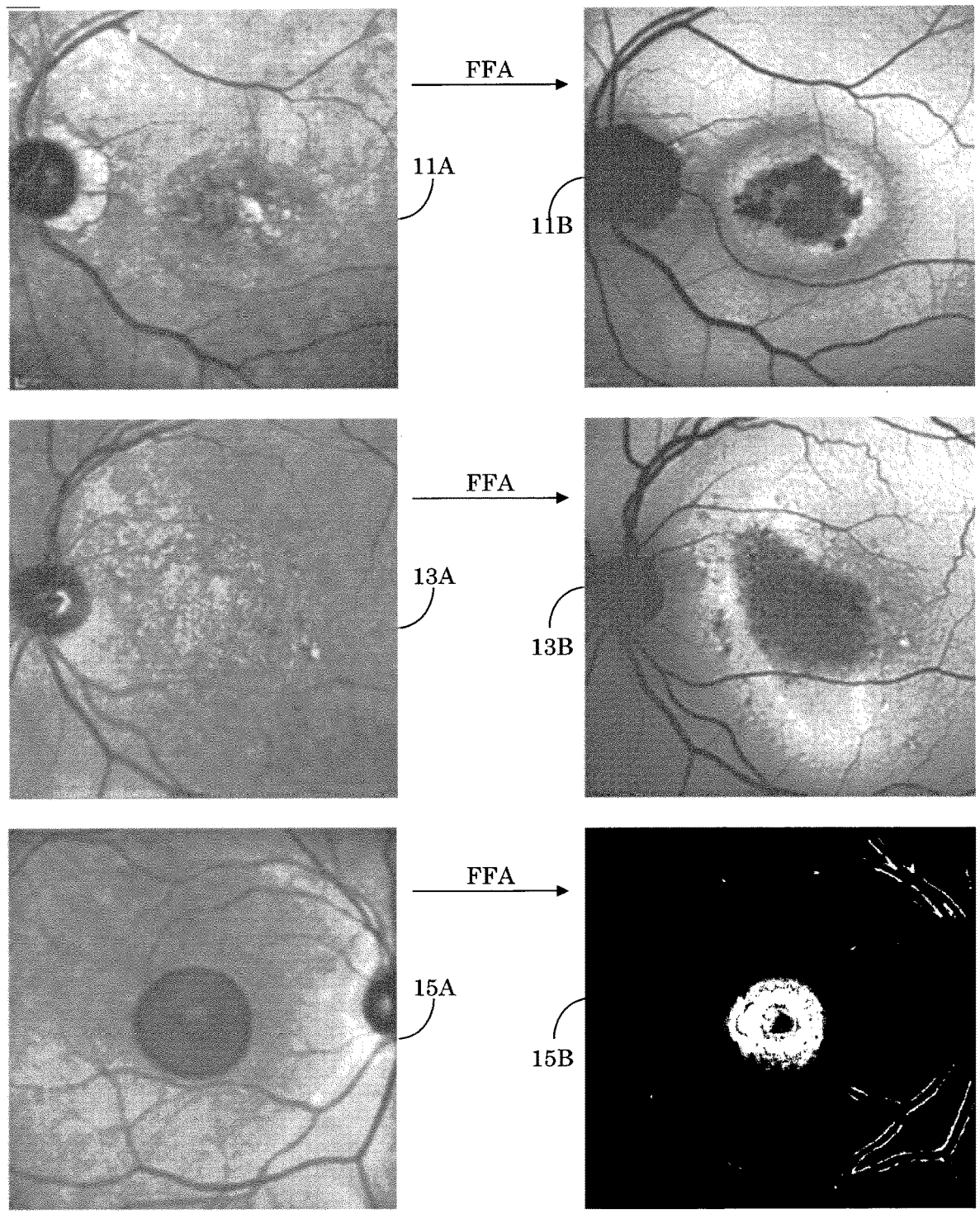
FIG. 1 provides three gray-scale images of true color images next to three corresponding autofluorescence image of a similar region of an eye.

Alternatively, high contrast images may be obtained without the use of fluorescent dye. For example, individual light sources that provide light at specific frequencies (e.g., colored LEDs or lasers) can be used to excite different, naturally occurring fluorophores in the eye in a technique known as autofluorescence. The resulting fluorescence can be detected by filtering out the excitation wavelength. This can make some features/tissues of the eye more easily discernable than is possible in a true color image. For example, fundus autofluorescence (FAF) imaging can be carried out with green or blue excitation which stimulates the natural fluorescence of lipofuscin, generating a monochrome image. For illustration purposes, FIG. 1 provides three gray-scale images 11A, 13A, and 15A of true color images next to three corresponding autofluorescence image 11B, 13B, and 15B of the same region of an eye. As is evident, some tissue features (e.g., in the central area of each image) that are not well defined in gray-scale images 11A, 13A, and 15A are easily identifiable in the corresponding autofluorescence images 11B, 13B, and 15B.

AMD generally starts as dry (atrophic) AMD and advances to wet (neovascular) AMD. Dry AMD is characterized by drusen (e.g., small white or yellowish deposits) that form on the retina (e.g., beneath the macula) causing it to deteriorate or degenerate over time. Early stage dry AMD may be treated by nutritional therapy or supplements, and wet AMD may be treated by injection (e.g. injections of Lucentis, Avastin, and Eylea), but there is currently no approved treatment for later stage dry AMD, although clinical trials are ongoing. Geographic atrophy (GA) is a late stage form of dry AMD, and is characterized by patches of cells in the retina that have degenerated or died off. GA may be defined as any sharply delineated round or oval region of hypopigmentation, or apparent absence of the retinal pigment epithelium (RPE), in which choroidal vessels are more visible than in surrounding areas, and is of a minimum size, such as 175 μm in diameter. Historically, color fundus images were used for imaging and identifying GA, however color fundus imaging cannot visualize lesion characteristics associated with GA progression. Due to the loss of RPE cells containing lipofuscin, an autofluorescent pigment, atrophic areas appears dark in fundus autofluorescence (FAF) imaging. This creates a high contrast between atrophic and non-atrophic areas, which can define areas of GA more easily than color fundus images. Use of autofluorescence has been found to be a more effective imaging modality for assessment of GA lesions, and monitoring changes in lesion structures. In particular, FAF with an excitation wavelength of 488 nm is a current, industry-preferred technology for morphological assessment of GA lesions. For illustration purposes, FIG. 2 provides an example FAF image of a GA region.

FAF images of GA may be characterized by abnormal patterns of hyper-autofluorescence surrounding atrophic regions. This has led to the classification, or identification, of specific phenotypes of GA. The classification of this characteristic hyper-autofluorescence into distinct patterns was first presented by Bindewald et al., in "Classification of Fundus Autofluorescence Patterns in Early Age-Related Macular Disease," *Invest Ophthalmol Vis Sci.*, 2005, 46:3309-14. Later, multiple studies were published documenting the impact of distinct phenotypic patterns on disease progression and their ability to serve as prognostic determinants, as discussed in: Holz F. G. et al., "Progression of Geographic Atrophy and Impact of Fundus Autofluorescence Patterns in Age-Related Macular Degeneration," *Am J. Ophthalmol*, 2007; 143: 463-472; Fleckenstein M. et al., "The 'Diffuse-Trickling' Fundus Autofluorescence Phenotype in Geographic Atrophy," *Invest Ophthalmol Vis Sci.*, 2014, 55:2911-20; and Jeong, Y. J. et al., "Predictors for the Progression of Geographic Atrophy in Patients with Age-Related Macular Degeneration: Fundus Autofluorescence Study with Modified Fundus Camera," Eye, 2014 online, 28(2), 209-218, DOI 10.1038/eye.2013.275. The above references are herein incorporated in their entirety by reference.

Of particular interest are 'diffused' (or 'diffuse-trickling') GA phenotype and 'banded' GA phenotypes, both of which have been empirically determined to be indicative of higher progression rate GA. Thus, in addition to identifying a GA region, proper phenotype classification of the identified GA region is likewise important. A 'diffused' GA region may be characterized by a degree of non-uniformity of its perimeter contour (e.g. a contour-non-uniformity measure above a predefined non-uniformity threshold). Consequently, it can be determined that the GA region of FIG. 2 is not of 'Diffused' phenotype since its contour is relatively uniform. By contrast, FIG. 3A provides some FAF image examples of GA lesions of 'diffused' phenotype, all of which demonstrate a high degree of contour non-uniformity. Since GA region may also have a high concentration of hyper-autofluorescence surrounding an atrophic region, a 'banded' GA region may be characterized by the amount of intensity variation in the hyper-autofluorescence along its perimeter. More specifically, if the variation in intensity of contour hyper-autofluorescence of a GA region is relatively uniform (e.g., an intensity-uniformity measure above a predefined intensity threshold), then the GA region may be characterized as 'banded' phenotype. For instance, it can be determined that the GA region of FIG. 2 is not of the 'banded' phenotype since it lacks uniformity of hyper-autofluorescence along its contour. By comparison, FIG. 3B provides an FAF example of a GA lesion of 'banded' phenotype with uniform hyper-autofluorescence along its contour.

Automatic quantification of GA lesion and its phenotype patterns could greatly aid in determining disease progression and clinical diagnosis of AMD. As mentioned above, there are currently a few segmentation algorithms for GA lesion assessment, but none of these address identifying and classifying different phenotypic patterns. That is, heretofore all segmentation methods available for GA lesions have lacked the ability to automatically classify distinct GA phenotypic patterns. Most of the segmentation methods reported in literature are semi-automated and require a manual input for segmentation of GA lesions. Moreover, all the previously reported segmentation methods were developed for use with standard field of view (FOV) images (e.g., a FOV of 45° to 60°), wherein the location of a GA lesion was generally limited to a predefined region of the standard FOV image. However, the recent increased interest in widefield images (e.g., having a FOV 60° to 120°, or more) has underscored a need for an automated GA assessment method suitable for use with widefield images. Use of widefield images complicates the use of typical GA segmentation algorithms since the location of a GA lesion cannot be limited to a predefined region of a widefield image, and some (physical) landmarks in diseased eyes may not be well defined.

Figure 4:
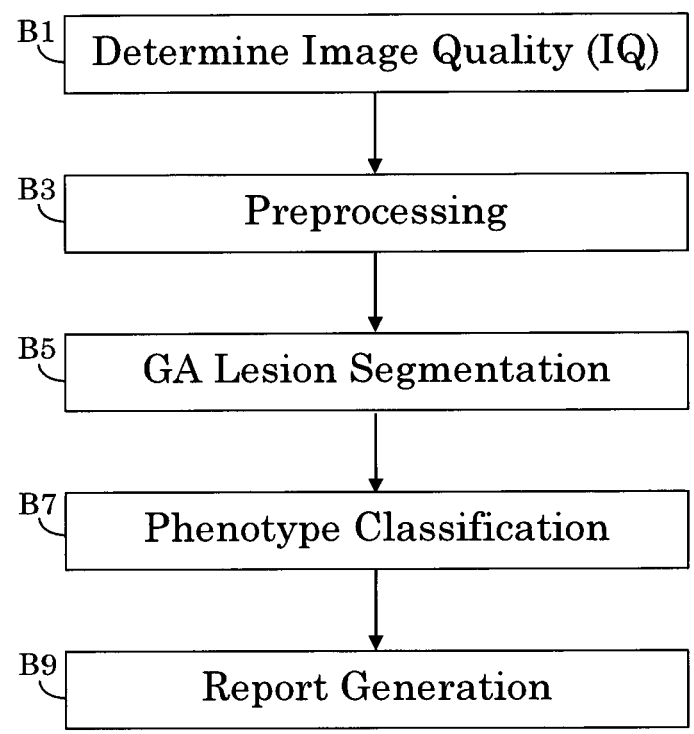
FIG. 4 provides a summary framework for automated segmentation and identification of GA phenotypic patterns.

FIG. 4 provides a summary framework for automated segmentation and identification of GA phenotypic patterns. First, a measure of image quality (IQ) is determined (block B1). This may include applying an image quality algorithm to the FAF image in order to reject images with non-gradable quality (an IQ measure below a predefined value). If the image is rejected, the process may skip directly to B9. If the IQ measure is sufficient to proceed with grading, the process continues to block B3.

Block B3 provides optional preprocessing to the FAF image. This may include optic disc and/or vessel detection, region of interest (ROI) selection, and histogram correction. Automatic ROI selection, which may be based on detection of the optic disc, limits the amount of pixels that need to be processed (e.g., classified) and thereby reduces the implementation time of the segmentation process.

Block B5 provides GA lesion segmentation. This may combine pixel-by-pixel classification and a modified Chan-Vese active contour. For example, classification may be provided by a machine learning (ML) model (e.g., support vector machine (SVM) and/or deep learning neural network) that provides initial GA segmentation. The GA segmentations are then submitted as starting points to a Chan-Vese active contour algorithm that further refines the GA segmentation. This hybrid process uses a novel combination of the supervised pixel classifier with active contour.

The GA segmentation(s) of block B5 may then be submitted to phenotype classification block B7, which identifies and classifies junctional zones near a GA segmented area (e.g., along the perimeter junction of a GA segmentation). For example, a set of random points equidistant from each other and distributed along the perimeter of a GA segmentation may be chosen. The distance of each chosen point to the centroid of the GA segmentation may then be calculated. These distances may then be used to determine a measure of perimeter contour smoothness of the GA segmentation (e.g. contour smoothness of the GA delineation). Intensity ridges and valleys may be calculated along a direction normal to the GA segmentation perimeter contour, outward, using, for example, Hessian filtered gradient derivatives and/or directional Gaussian filter. This may provide a measure of light intensity regularity along the perimeter of the GA segmentation. Both of these parameters may be used to classify the junctional zone phenotypes. For example, the measure of contour smoothness of the GA segmentation may be used to identify a 'diffused' phenotype, and the measure of intensity regularity of the GA segmentation may be used to identify a 'banded' phenotype.

Alternatively a (e.g., deep learning) neural network may be implemented as block B7. In this case, the neural network may be trained to receive the GA segmentation(s) of block B5 and classify the specific phenotype (e.g., diffused or banded) of each GA segmentation. Further alternatively, a neural network may be trained to do the function of GA lesion segmentation block B5 and phenotype classification block B7. For example, a set of images showing GA regions delineated by experts and their respective phenotypes, as identified by experts, may be used as a training output set for the neural network, and the original not-delineated images may be used as a training input set for the neural network. The neural network may thereby be trained to not only segment (or delineate) GA lesion regions, but also to identify their respective phenotypes (e.g., 'diffused' or 'banded').

Additionally, it has been found that retinal vessels may lead to incorrectly identifying some fundus regions as GA segmentation. This may be avoided by removing retinal vessels (e.g., the retinal vessels identified in preprocessing block B3) from the FAF image prior to application of GA segmentation, e.g. prior to block B5. In this case, the retinal vessels may optionally be removed from the training images used to train the learning model (SVM or neural network).

Final block B9 generates a report summarizing the results of the present framework. For example, the report may state whether the image quality was too low for grading, specify if the identified GA lesions are of the 'high' progression rate type, specify the phenotype of the GA lesion, and/or recommend a follow-up examination date. Both the 'diffused' and 'banded' phenotypes have been empirically determined to be indicative of high progression rate GA; although the 'diffused' phenotype may have higher progression rate than the 'banded' phenotype. The follow-up examination date recommendation may be based on the determination of GA lesion type. For example, a higher progression type GA lesion may warrant an earlier follow-up examination date than a lower progression or 'low' (or non-high) progression type GA lesion.

Figure 5:
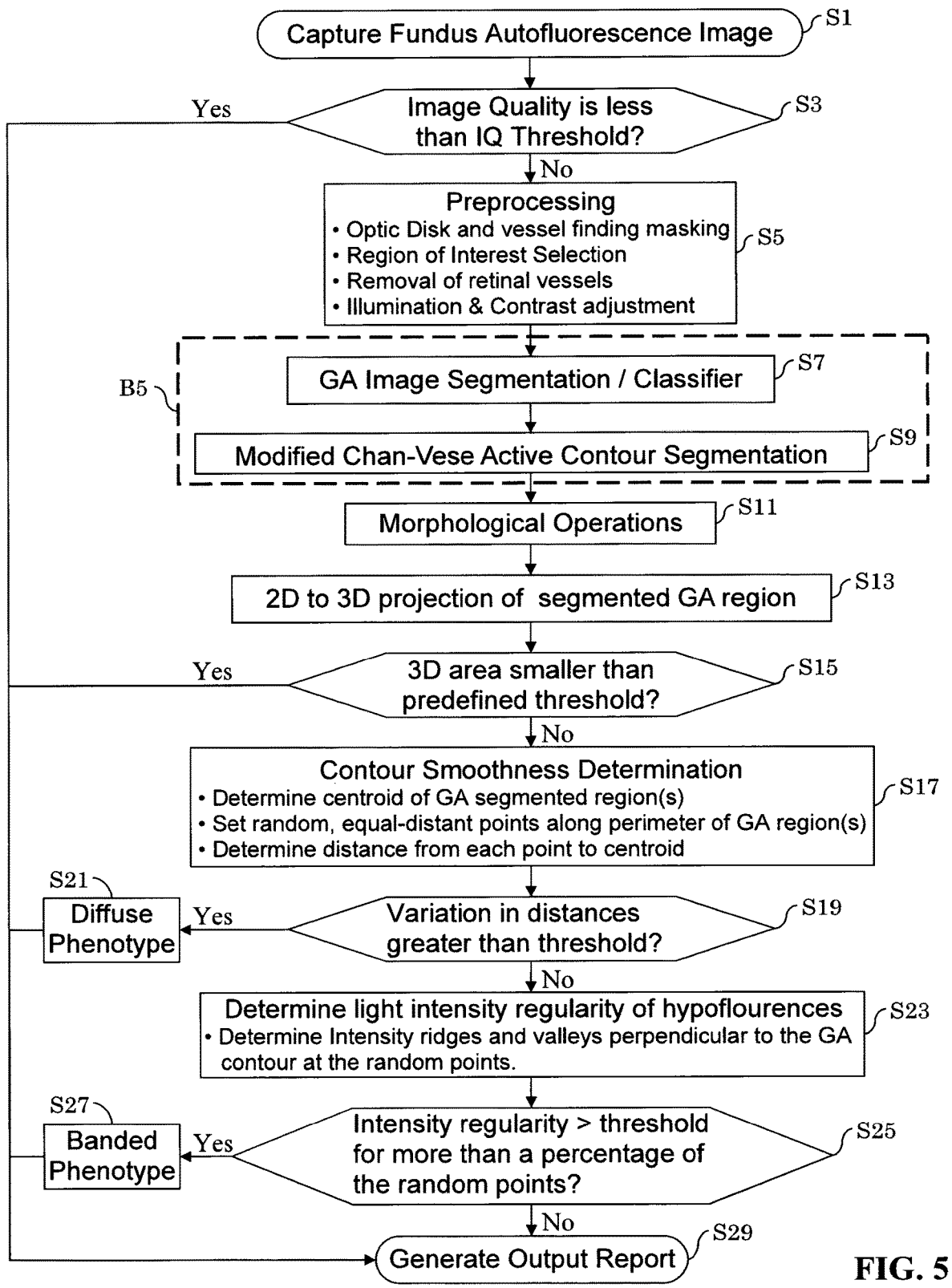
FIG. 5 illustrates a more detailed process for automated segmentation and identification of GA phenotypic patterns in accord with the present invention.

FIG. 5 illustrates a more detailed process for automated segmentation and identification of GA phenotypic patterns in accord with the present invention. For illustration purposes, the present invention is described as applied to widefield FAF images, but may equally be applied to other types of ophthalmic imaging modalities, such as OCT/OCTA that can generate images that provide visualization of GA. For example, it may be applied to an en face OCT/OCTA image. The present imaging system and/or method may begin by capturing, or otherwise acquiring (e.g., by accessing a data store of), fundus autofluorescence images (step S1). An assessment (e.g., measure) of image quality of the acquired fundus autofluorescence images is then made using any suitable image quality (IQ) algorithm known in the art. For example, the measure of image quality may be based on one, or a combination, of quantifiable factors, such as sharpness, noise, dynamic range, contrast, vignetting, etc. If the measure of image quality is less than a predefined image quality threshold (step S3=Yes), then it is determined that the FAF image is not suitable for further analysis and the process proceeds to step S29, where a report is generated stating that no GA segmentation or quantification can be made on the current FAF image. In essence, the image quality IQ algorithm is applied to reject images with non-gradable quality. If the image quality is not less than the minimum threshold (step S3=No), then the process may proceed to an optional preprocessing step S5, or may alternatively proceed directly to a GA image segmentation step S7.

Preprocessing step S5 may include multiple preprocessing sub-steps. For example, it may include an optic disc and/or vessel detection (e.g., a finding mask), as well as identifying the image as being from a patient's left or right eye. As explained above, physical landmarks may be difficult to identify in diseased eyes, but the optic disc may be identified by the concentration of vessel structures emanating from it. For example, a machine learning model (e.g., deep learning neural network, such as discussed below) may be trained to identify an optic disc in a widefield image. Alternatively, another type of machine learning model (e.g., a support vector machine) may be trained to identify the optic disc, such as by correlating the location of the optic disc to a location with an origin of a concentration of vascular structures. In either case, additional information, external to the image, may be used in training, such as information provided by an electronic medical record (EMR) or by the Digital Imaging and Communications in Medicine (DICOM) standard.

As stated above, it has been found that retinal vessels may lead to false positives in GA segmentation. Therefore, preprocessing may further include identification and removal of retinal vessels prior to application of GA segmentation so as to mitigate the number of false positives, e.g., reduce the identification of false GA regions. As stated above, GA segmentation may be based on a machine learning model, and retinal vessels may be removed from its training set of images. For example, a neural network may be trained using a training output set of eye fundus images (e.g., FAF images) with manually delineated GA regions and manually identified phenotypes, and using a training input set of the same eye fundus images without the manually delineated GA regions and without the identified phenotypes. If in an operational phase (or test phase) the neural network is to accept an input test image whose retinal vessels have been removed, then the neural network may be trained with training images whose retinal vessels have also been removed. That is, retinal vessels may be removed from the fundus images in training input set and training output set prior to training the neural network.

Preprocessing step S5 may also include region of interest (ROI) selection to limit processing (including GA segmentation) to the identified ROI within the FAF image. Preferably, the identified ROI would include the macula. ROI selection may be automated based on the landmark detection (optic disc and retinal vessels), image size, image entropy and fundus scan information extracted from DICOM, etc. For example, depending upon whether the image is of a left or right eye, the macula would be to the right or left of the optic disc location within the image. As it would be understood, ROI selection limits the amount of pixels that need to be classified (e.g., for GA segmentation) and thereby reduces the implementation time of the present process/method.

Preprocessing step S5 may further include illumination correction and contrast adjustment. For example, uneven image illumination may be corrected by using background subtraction, and image contrast may be adjusted by using histogram equalization.

The preprocessed images are then submitted to a two-stage lesion segmentation (e.g., block B5 of FIG. 4) that includes GA segmentation and active contour analysis. The first stage in block B5 is a GA segmentation/classifier stage (S7) that is preferably based on machine learning and identifies one or more GA regions, and the second stage in block B5 is an active contour algorithm applied to the identified GA regions. The GA segmentation stage S7 may provide GA classification on a sub-image sector by sub-image sector basis, where each sub-image sector may be one pixel (e.g. on a pixel-by-pixel basis) or each sub-image sector may be a group (e.g., window) of multiple pixels. In this manner, each sub-image sector may be individually classified as a GA-sub-image or a non-GA-sub-image. The active contour analysis stage S9 may be based on the known Chan-Vere algorithm. In the present case, the Chan-Vese algorithm is modified to change energy and movement direction of contour growth. For example, region based image characteristics are used to dictate the contour movement. Essentially, segmentation block B5 for GA lesions uses a hybrid process that combines (for example, pixel-by-pixel) classification and Chan-Vese active contour. Optionally, this proposed hybrid algorithm uses a novel combination of the supervised (e.g., pixel) classifier (S7) with a geometric active contour model (S9). As it would be understood by one versed in the art, a geometric active contour model typically begins with a contour (e.g., a starting point) in an image plane defining an initial segmentation, and then evolves the contour according to some evolution equation so as to stop on the boundaries of a foreground region. In the present case, the geometric active contour model is based on a modified Chan-Vese algorithm.

GA segmentation/classifier stage (S7) is preferably based on machine learning, and may be implemented, for example, by use of a support vector machine or by a (deep learning) neural network. Each implementation is separately described herein.

Generally, a support Vector Machine, SVM, is a machine learning, linear model for classification and regression problems, and may be used to solve linear and non-linear problems. The idea of an SVM is to create a line or hyperplane that separates data into classes. More formally, an SVM defines one or more hyperplanes in a multi-dimensional space, where the hyperplanes are used for classification, regression, outlier detection, etc. Essentially, an SVM model is a representation of labeled training examples as points in multi-dimensional space, mapped so that the labeled training examples of different categories are divided by hyperplanes, which may be thought of as decision boundaries separating the different categories. When a new test input sample is submitted to the SVM model, the test input is mapped into the same space and a prediction is made regarding what category it belongs to based on which side of a decision boundary (hyperplane) the test input lies.

In a preferred embodiment, an SVM is used for image segmentation. Image segmentation aims to divide an image into different sub-images with different characteristics and extract objects of interest. More specifically in the present invention, an SVM is trained to segment GA regions in FAF images (e.g., trained to clearly define the contours of GA regions in an FAF image). Various SVM architectures for image segmentation are known in the art, and the specific SVM architecture(s) used for this task is not critical to the invention. For example, a least squares SVM may be used for image segmentation based on pixel-by-pixel (or sub-image sector by sub-image sector) classification. Both pixel-level features (e.g., color, intensity, etc.) and texture features may be used as inputs to the SVM. Optionally, an ensemble of SVMs, each providing specialized classification, may be linked to achieve better results.

Thus, initial contour selection may be made using an SVM classifier (e.g., by SVM model-based segmentation). Preferably, Haralick texture features, mean intensity and variance parameters obtained from gray-level co-occurrence matrices (e.g., an 11×11 window moving within a region of interest) are used to train a SVM classifier. As explained above, retinal vessels may optionally be removed from the training images. Irrespective, feature extraction is limited to a specific ROI (e.g., the ROI selected in step S5), which results in better time performance than applying GA segmentation/classification to the whole image. In this manner, the SVM provides an initial contour selection (e.g., provides an initial GA segmentation as a starting point) for submission to the active contour algorithm of step S9 for better performance. Evolution time of the active contour algorithm is heavily dependent on the initial contour selection, as is explained, for example, in "Semi-automatic geographic atrophy segmentation for SD-OCT images" by Chen, Q. et al., *Biomedical Optics Express*, 4(12), 2729-2750, herein incorporated by reference in its entirety.

The SVM classifier was tested and compared for performance. Expert graders manually delineated GA regions in FAF images not used in training, and the results were compared with segmentation results by the SVM model. FIG. 6 shows four GA regions delineated by human experts, and FIG. 7 shows corresponding GA delineation (e.g., the perimeter of GA segmentation) provided by the present SVM. As shown, the SVM model agrees well with the manual GA segmentation provided by the expert graders.

GA segmentation/classifier stage (S7) may also be implemented by use of a neural network (NN) machine learning (LM) model. Various examples of neural networks are discussed below with reference to FIGS. 16 to 19, any, or a combination, of which may be used with the present invention. An exemplary implementation of a GA segmentation/classifier using a deep learning neural network was constructed based on the U-Net architecture (see FIG. 19). In this case, the NN was trained using manually segmented images (e.g., images with GA regions segmented by human experts) as training outputs and corresponding non-segmented images as training inputs.

In an example implementation, 79 FAF-Green images were obtained from 62 patients with GA using the CLARUS™ 500 fundus camera (ZEISS, Dublin, CA). These 79 FAF images were divided into 55 FAF images for training and 24 FAF images for testing. Optionally, retinal vessels may be removed from the training and/or testing images. Data augmentation methods were used to increase the size of the training data and generated 880 (image) patches of size 128×128 pixels for training. In the present U-Net, the contracting path consisted of four convolutional neural network (CNN) blocks, and each CNN block consisted of 2 CNN layers followed by one max pooling layer. The bottleneck (e.g. the block between the contracting path and the expanding path) consisted of 2 CNN layers with optional 0.5 inverse dropout to avoid overfitting issues. The expanding path of a U-net is typically symmetric to the contracting path, and herein consisted of four CNN blocks following the bottleneck. Each CNN block in the expanding path consisted of a deconvolution layer and a concatenation layer followed by 2 CNN layers. The last CNN block (e.g., the fourth CNN block) in this expanding path provides a segmentation output, which may be fed to an optional classification layer for labeling. This final classifier formed the last layer. The present implementation used a custom dice coefficient loss function for training the machine learning model, but other loss functions, such as the cross-entropy loss function may also be used. The segmentation performance of the DL ML model may be fine-tuned by using post-learning optimization. For example, a method named 'Icing on the Cake' may be used, which trains only the final classifier (i.e., the last layer) again after the initial (ordinary) training is complete.

The DL approach was compared with manually segmented GA regions. FIG. 8 shows five GA regions manually delineated by expert graders, and FIG. 9 shows the corresponding GA delineation provided by the present DL machine model. For evaluation purposes, fractional area difference, overlap ratio, and Pearson's correlation between measured areas were determined. The fractional area difference between GA regions generated by the DL machine model and the manual segmentation was 4.40%±3.88%. Overlap ratio between manual and DL automatic segmentation was 92.76±5.62, and correlation of GA areas generated by the DL algorithm and the manual grading was 0.995 (p-value<0.001). Thus, quantitative and qualitative evaluations demonstrate that the proposed DL model for segmenting GA in FAF images shows very strong agreement with expert manual grading.

Thus, as is evident from FIGS. 6-9, both SVM-based and DL-based classification provide good, initial GA delineation, or segmentation.

The GA segmentation results from step S7 may be submitted as an initial contour selection(s) to the active contour algorithm (step S9). The present embodiment uses a modified Chan-Vese (C-V) active contour segmentation algorithm. In general, an active contour algorithm has been used for GA segmentation in optical coherence tomography (OCT) images, as described in "Automated geographic atrophy segmentation for SD-OCT images using region-based C-V model via local similarity factor" by Niu, S. et al., Biomedical Optics Express, 2016 Feb. 1, 7(2), 581-600, herein incorporated in its entirety by reference. In the present case, however, Chan-Vese active contour segmentation is used as a second phase in a two-part segmentation process. The initial contours provided by the SVM or DL learning model classifier(s) are close to the expert annotated GA boundaries. This reduces the execution time for the Chan-Vese active contour segmentation and improves its performance.

The final GA segmentation results, provided by two-stage segmentation block B5, may optionally be submitted to additional, morphological operations (step S11) to further refine the segmentation. Morphological operations (e.g., erosion, dilation, opening and closing) are applied to the output of Chan-Vese active contour to refine the contour boundaries and to remove small isolated regions.

Next, the size of the segmented GA is determined. Since the GA segmentation is from a 2D image, but the eye fundus is curved, the 2D GA segmentation may be mapped to a 3D space (step S13) and the measurement may be made in the 3D space to account for distortions and obtain a more accurate area measure. Any suitable method of mapping from 2D pixels to 3D coordinates based on known imaging geometry may be used. For example, a method well-known in the art for mapping pixels in a 2D image plane onto points on a sphere (e.g., a 3D space) is stereographic projection. Other examples of 3D reconstruction from 2D fundus images are provide in "3D Reconstruction of Human Retina from Fundus Image—A Survey", by Cheriyan, J. et al., international Journal of Modern Engineering Research, Vol. 2, Issue. 5, September-October 2012 pp-3089-3092, herein incorporated in its entirety by reference.

Determining a GA size measurement in a 3D space may make use of additional information provided by an ophthalmic imaging system, if available. For example, some ophthalmic imaging systems store 3D positions in an array along with the 2D coordinates of each pixel position in the 2D image. This methodology may be included with the Digital Imaging and Communications in Medicine (DICOM) standard Wide Field Ophthalmic Photography Image Module. Alternatively or in combination, some systems may store a model that can be run on an arbitrary set of 2D positions to generate the relevant 3D position.

If the determined area in 3D space is smaller than a predefined threshold (step S15=Yes), then the GA segmentation is determined to be too small to be a true GA lesion and processing proceeds to step S29 to generate a report. If the determined area is not smaller than the predefined threshold, e.g. 96K $\mu m^2$, (step S15=No), then the GA segmentation is accepted as true GA lesion and the process attempts to identify the phenotype of the identified GA segmentation.

Figure 10:
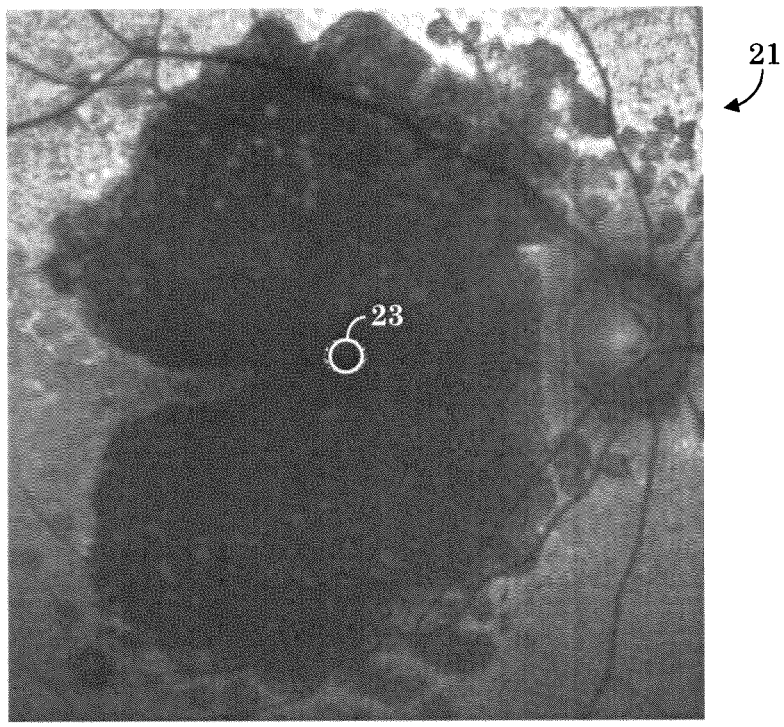
FIG. 10 illustrates a 'diffused' phenotype GA region with its centroid indicated by a circle.
Figure 11:
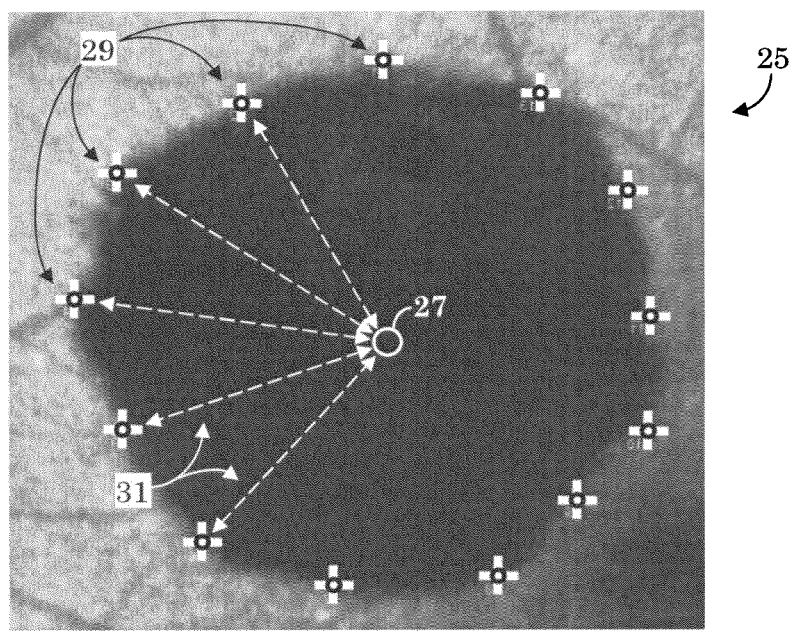
FIG. 11 illustrates a 'banded' phenotype GA region with a centroid and a set of thirteen random points equally spaced along the perimeter of the GA segmentation.

A first step in identifying the phenotype may be to analyze contour smoothness of the GA segmentation (step S17). This may include several sub-steps. To identify and classify junctional zones near GA segmented area (e.g., along the edge of a GA segmented area), one may begin by determining the centroid of the GA segmented region. This centroid calculation may be applied to the 2D image representation of the GA segmented region. FIG. 10 illustrates a diffused phenotype GA region 21 with its centroid indicated by a circle 23. A next step may be to identify a set of random points, equally spaced along the perimeter of the GA segmentation. FIG. 11 illustrates a banded phenotype GA region 25 with a centroid 27 and a set of thirteen random points 29 (each identified as the center of white crosshairs) equally spaced along the perimeter of the GA segmentation. It is to be understood that thirteen is an exemplary value and any number of points sufficient to circumnavigate the perimeter of GA region may be used. The distances from each point 29 to the centroid 27 are then calculated (e.g., linear distances 31). The variation in the distances 31 is used to differentiate 'diffuse' phenotype from others, such as 'banded' phenotype.

In step S19, if the variation in distances is greater than a distance-variation threshold, (step S19=Yes), then the GA region is identified as being a 'diffused phenotype' (step S21), and the process proceeds to step S29 where a report is generated. This variation in distance, or contour-non-uniformity measure, may be determined as the average distance variation for a current GA segmentation, and the distance-variation threshold may be defined as 20% of a standardized mean variation of (e.g., diffused) GA segments. the standardized mean variation may be determined from a library of GA segments, e.g., a (standardize) library of FAF images of GA lesions. However, if the variation in distance is not greater than the distance-variation threshold (step S19=No), then processing proceeds to step S23).

In step S23, intensity ridges and valleys are determined for (at least a fraction of) the set of random points 29 along a direction perpendicular to the GA contour. This may be done using Hessian filtered gradient derivatives and/or a directional Gaussian filter. If ridges and valleys (light intensity regularity-hypoflourences) above a preset intensity-variation threshold are present for more than a predefined percentage (e.g., 60%) of chosen points 29, (step S25=Yes), the image (e.g., the GA segmentation) is classified as 'banded' phenotype (step 27), and the process proceeds to step S29 where a report is generated. The intensity ridges and valleys may define an intensity variability measure, and the intensity-variation threshold may be defined as 33% of a standardized mean intensity-variation of (e.g., banded) GA segments. This standardized mean intensity-variation may be determined from a library of GA segments, e.g., a (standardize) library of FAF images of GA lesions. If the light intensity regularity-hypoflourences is not greater than the present intensity-variation threshold (step S25=No), then no determination of phenotype can be made and processing proceeds to step S29.

As stated above, a neural network may be trained to provide GA segmentation, as described above in reference to step S7. However, a neural network, such as the U-Net of FIG. 19, may also be trained to provide phenotype classification. For example, by providing expert labeling of the specific phenotype of each expert delineated GA lesion segmentation in a training image set, the neural network may be trained to provide phenotype classification along with, or in addition to, GA legion segmentation identification. In this case, the phenotype identification/classification steps associated with step S17 to S25 may be omitted and provided by the neural network. Alternatively, the phenotype classification provided by the neural network may be combined with the phenotype identification results of steps S17 to S25, such as by a weighted average.

Step S29 generates a report summarizing the results of the present process. For images with non-gradable IQ (step S3=Yes), image quality alone is reported, and for other images the report generated will have one or more of the following:

a. GA segmented area measurement of the current visit.
b. Junctional zone phenotype of the current GA (if available).
c. Risk of progression (e.g., risk of progression reported as high for 'banded' and 'diffuse' phenotypes).
d. Suggested follow-up visit time.

Figure 12:
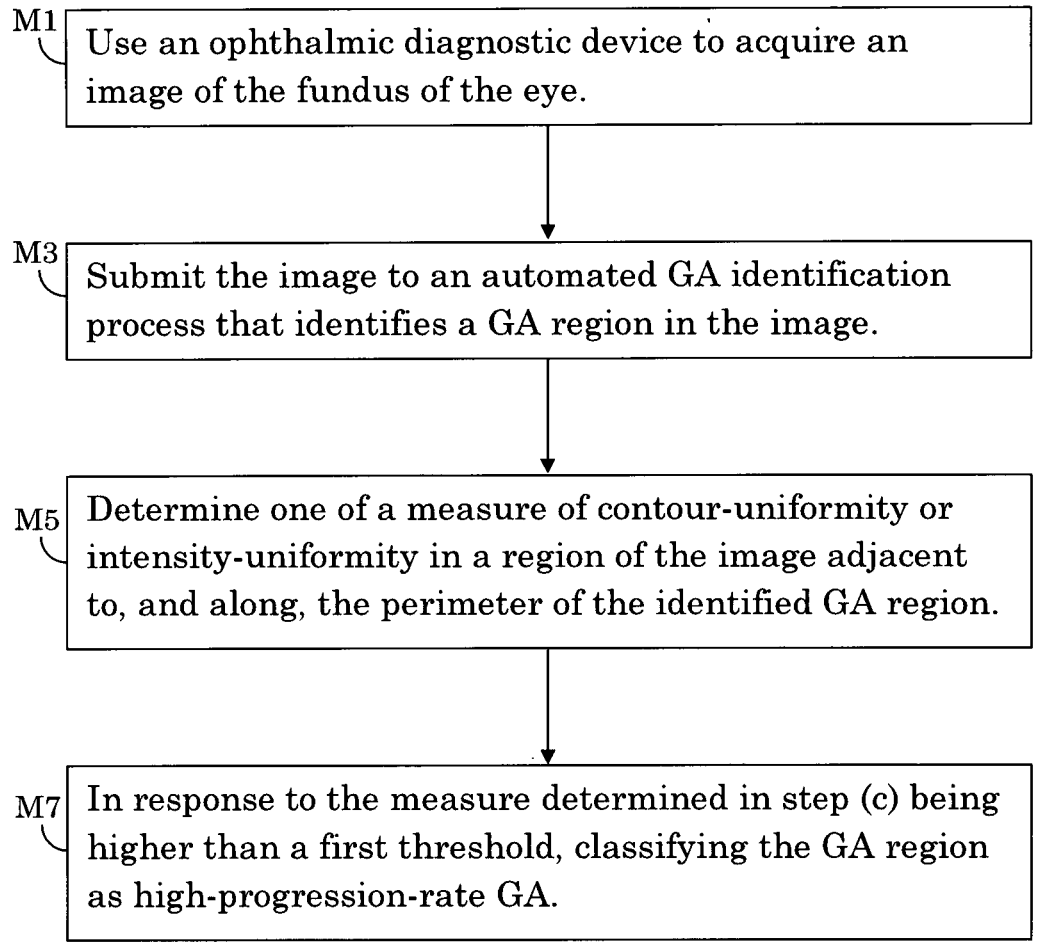
FIG. 12 illustrates an example method for automatically classifying geographic atrophy in an eye.

FIG. 12 illustrates another example method for automatically classifying geographic atrophy (GA) in an eye. In the present example, rather than checking for every specific GA phenotype in a library of phenotypes (e.g., 'diffused' phenotype and 'banded' phenotype), the present method may stop classifying a current GA region as soon the current GA region is identifying as any phenotype associated with a high progression rate (e.g., an empirical association). The current GA region may then simply be classified as a "high-progression-rate" GA without specifying its specific GA phenotype. Optionally if desired, such as by use of a user input via a graphical user interface (GUI), the process may proceed to classify the current GA segmentation as one or more specific phenotype. In this case, the method may further identify a "high-progression-rate" GA as being a 'diffused' phenotype or 'banded' phenotype. Optionally, the method may order the search for GA phenotypes according to which phenotypes are more prevalent in a particular population (e.g., to which a patient may belong), or ordered the search based on which phenotypes have been (e.g. empirically) determined be associated with higher progression rate GA than others. For example, 'diffused' phenotype GA may be considered to have a higher progression rate than 'banded' phenotype GA based on empirical observations, and so the method may check if a current GA segmentation is of the 'diffused' phenotype first, and check for 'banded' phenotype second only if the current GA segmentation is determined to not be of 'diffused' phenotype.

The method may begin at method step M1 by using an ophthalmic diagnostic device to acquire an image of the fundus of the eye. The image (e.g., an autofluorescence image or en face image) may be generated by a fundus imager or an OCT. The ophthalmic diagnostic device may be the device that generates the image, or may alternatively be a computing device that accesses the image from a data store of such image over a computer network (e.g., the Internet).

In method step M3, the acquired image is submitted to an automated GA identification process that identifies a GA region in the image. The automated GA identification process may include a GA segmentation process, as is known in the art. The preferred segmentation process, however, is a two-step segmentation that combines GA classification (e.g., pixel-by-pixel) with active contour segmentation. The first of this two-step process may be a trained, machine model, such as a SVM or a (e.g., deep learning) neural network that segments/classifies/identifies GA regions within the image.

For example, a neural network based on the U-Net architecture may be used, where its training set may include a training output set of expertly demarcated fluorescence images and a training input set of corresponding, non-demarcated fluorescence images. Irrespective of the type of GA segmentation/classification used in this initial stage, the identified GA segmentations may be submitted as starting points to an active contour algorithm (e.g., Chan-Vese segmentation) to further refine the GA segmentation. Optionally, the results may be submitted to Morphological operations (e.g., erosion, dilation, opening and closing) to further clean the segmentation before proceeding to the next method step M5.

Optionally, before proceeding with step M5, the final GA segmentation(s) from step M3 may be mapped to a three-dimensional space representative of the shape of the eye's fundus, and the area of the mapped GA determined. If the area is smaller than a predefined threshold, then the GA segmentation may be re-classified as non-GA and removed from further processing. Assuming that the identified GA segmentation is large enough to qualify as a true GA region, processing may proceed to step M5.

Method step M5 analyzes the identified GA regions by determining one or two different measures, each designed to identify one of two different GA phenotypes associated with high-progression-rate GA. More specifically, a contour-non-uniformity measure may be used to identify 'diffused' phenotype GA and an intensity-uniformity measure may be used to identify 'banded' phenotype GA. If a first determined measure confirms either "diffused" phenotype GA or 'banded' phenotype GA (e.g., the measure is higher than a predefined threshold), then method step M7 classifies the identified GA region as "high-progression-rate" GA. If the first determined measure does not confirm one of 'diffused' or 'banded' phenotype, then the second measure may be determined to check if the other of the two phenotypes is present. If the other phenotype is present, then the identified GA region may again be classified as "high-progression-rate" GA. Optionally, or alternatively, method step M7 may specify the specific phenotype classification ('diffused' or 'banded') identified for the GA region.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two dimensional area such a slit or broad line.

Figure 13:
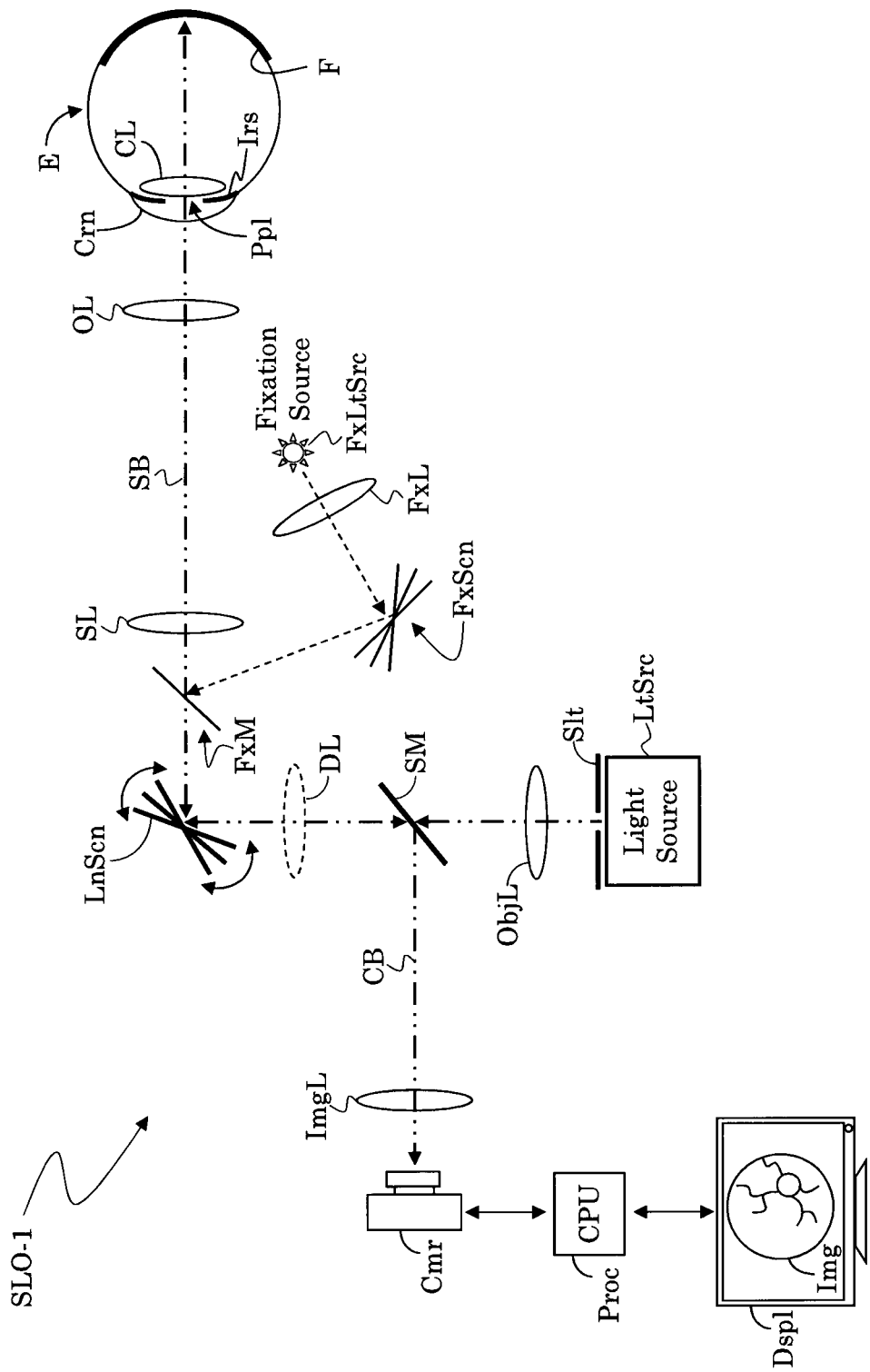
FIG. 13 illustrates an example of a slit scanning ophthalmic system for imaging a fundus.

FIG. 13 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Cm, iris Irs, pupil Ppl, and crystalline lens CL) to be scanned across the fundus F. In the case of a flood fundus imager, no scanner is needed and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state of the art lenses including but not limited to refractive, diffractive, reflective, or hybrid lenses/systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may focus the scanning line beam SB onto the fundus F (or retina) of eye E and image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (4-$f$ configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system shown in FIG. 20). Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/

0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 13. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three color images can be combined to display the true color image or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared (IR) reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green angiography (ICG) imaging can be accomplished by collecting images after a fluorescent dye has been injected into the subject's bloodstream.

Optical Coherence Tomography Imaging System

In addition to fundus photography, fundus auto-fluorescence (FAF), fluorescein angiography (FA), ophthalmic images may also be created by other imaging modalities, such as, optical coherence tomography (OCT), OCT angiography (OCTA), and/or ocular ultrasonography. The present invention, or at least portions of the present invention with minor modification(s) as it would be understood in the art, may be applied to these other ophthalmic imaging modalities. More specifically, the present invention may also be applied to ophthalmic images produces by an OCT/OCTA system producing OCT and/or OCTA images. For instance, the present invention may be applied to en face OCT/OCTA images. Examples of fundus imagers are provided in U.S. Pat. Nos. 8,967,806 and 8,998,411, examples of OCT systems are provided in U.S. Pat. Nos. 6,741,359 and 9,706,915, and examples of an OCTA imaging system may be found in U.S. Pat. Nos. 9,700,206 and 9,759,544, all of which are herein incorporated in their entirety by reference. For the sake of completeness, an exemplary OCT/OCTA system is provided herein.

Figure 14:
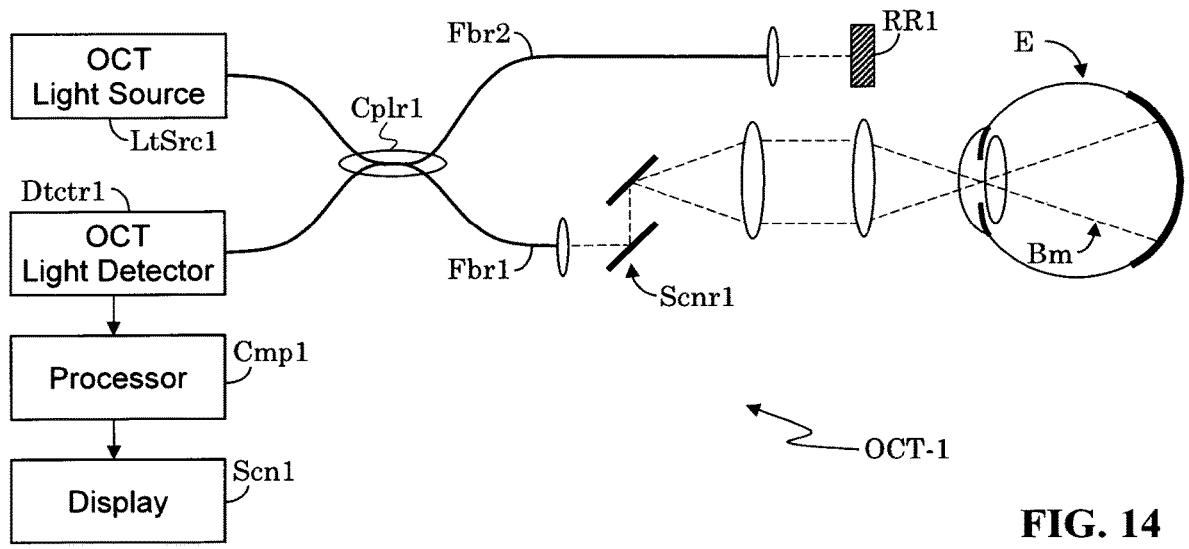
FIG. 14 illustrates a generalized frequency domain optical coherence tomography system used to collect 3-D image data of the eye suitable for use with the present invention.

FIG. 14 illustrates a generalized frequency domain optical coherence tomography (FD-OCT) system used to collect 3-D image data of the eye suitable for use with the present invention. An FD-OCT system OCT_1 includes a light source, LtSrc1. Typical light sources include, but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 can be either a broadband light source with short temporal coherence length in the case of spectral domain OCT (SD-OCT) or a wavelength tunable laser source in the case of swept source OCT (SS-OCT). The light may be scanned, typically with a scanner Scnd between the output of the optical fiber Fbr1 and the sample E, so that the beam of light (dashed line Bm) is scanned laterally (in x and y) over the region of the sample to be imaged. In the case of a full-field OCT, no scanner is needed and the light is applied across the entire, desired field of view (FOV) at once. Light scattered from the sample is collected, typically into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, typically in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor Cmp1 (e.g., computing device) that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument or functions may be performed on an external processing unit (e.g., the computer system shown in FIG. 20) to which the collected data is transferred. This unit could be dedicated to data processing or perform other tasks which are quite general and not dedicated to the OCT device. The processor Cmp1 may contain, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that performs some, or the entire data processing steps, prior to passing on to the host processor or in a parallelized fashion.

The sample and reference arms in the interferometer could consist of bulk-optics, fiber-optics, or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" Optics Letters 36(13): 2390 2011; Y. Nakamura, et al, "High-Speed three dimensional human retinal imaging by line field spectral domain optical coherence tomography" Optics Express 15(12):7103 2007; Blazkiewicz et al, "Signal-to-noise ratio study of full-field Fourier-domain optical coherence tomography" Applied Optics 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|ei\varphi$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meets predefined criteria may be identified as blood flow. A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross sectional image that includes the z-dimension.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 15:
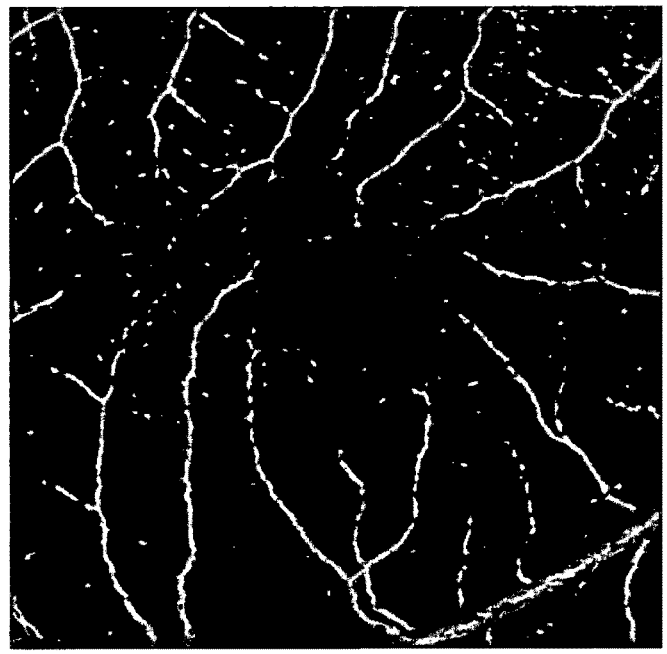
FIG. 15 shows an example of an en face vasculature image.

FIG. 15 shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature.

Neural Networks

As discussed above, the present invention may use a neural network (NN) machine learning (ML) model. For the sake of completeness, a general discussion of neural networks is provided herein. The present invention may use any, singularly or in combination, of the below described neural network architecture(s). A neural network, or neural net, is a (nodal) network of interconnected neurons, where each neuron represents a node in the network. Groups of neurons may be arranged in layers, with the outputs of one layer feeding forward to a next layer in a multilayer perceptron (MLP) arrangement. MLP may be understood to be a feedforward neural network model that maps a set of input data onto a set of output data.

Figure 16:
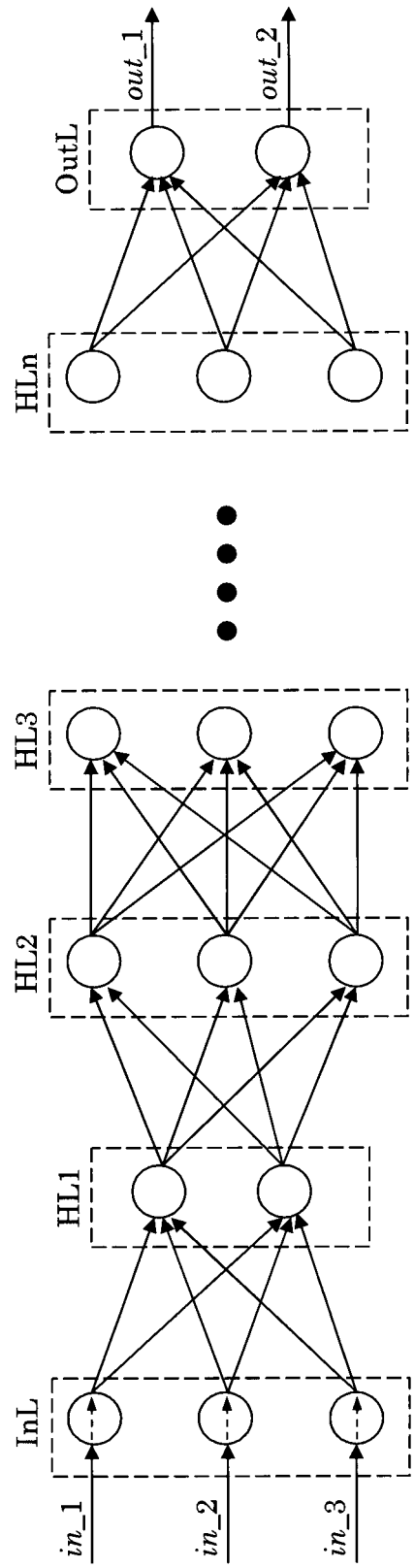
FIG. 16 illustrates an example of a multilayer perceptron (MLP) neural network.

FIG. 16 illustrates an example of a multilayer perceptron (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any given number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output that is fed forward to neurons in the layer immediately following it. But each neuron in a hidden layer may receive multiple inputs, either from the input layer or from the outputs of neurons in an immediately preceding hidden layer. In general, each node may apply a function to its inputs to produce an output for that node. Nodes in hidden layers (e.g., learning layers) may apply the same function to their respective input(s) to produce their respective output (s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 17:
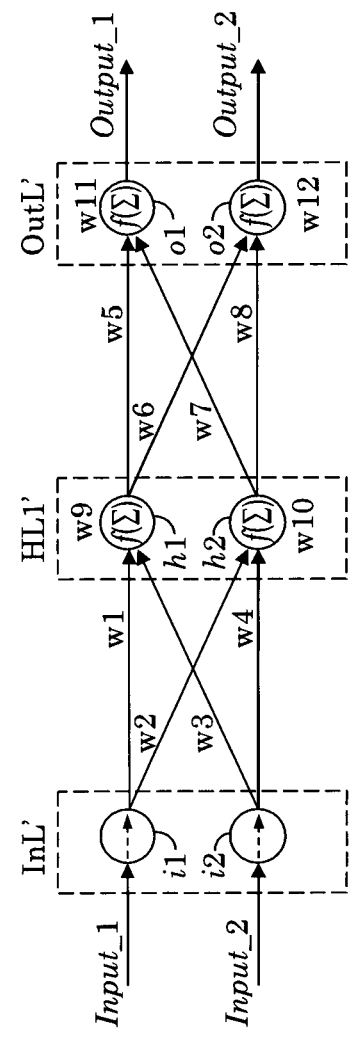
FIG. 17 shows a simplified neural network consisting of an input layer, a hidden layer, and an output layer.

For illustration purposes, FIG. 17 shows a simplified neural network consisting of an input layer InL', a hidden layer HL1', and an output layer OutL'. Input layer InL' is shown having two input nodes i1 and i2 that respectively receive inputs Input_1 and Input_2 (e.g. the input nodes of layer InL' receive an input vector of two dimensions). The input layer InL' feeds forward to one hidden layer HL1' having two nodes h1 and h2, which in turn feeds forward to an output layer OutL' of two nodes o1 and o2. Interconnections, or links, between neurons (illustrative shown as solid arrows) have weights w1 to w8. Typically, except for the input layer, a node (neuron) may receive as input the outputs of nodes in its immediately preceding layer. Each node may calculate its output by multiplying each of its inputs by each input's corresponding interconnection weight, summing the products of it inputs, adding (or multiplying by) a constant defined by another weight or bias that may be associated with that particular node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known the art, and selection of a specific activation function is not critical to the present discussion. It is noted, however, that operation of the ML model, or behavior of the neural net, is dependent upon weight values, which may be learned so that the neural network provides a desired output for a given input.

The neural net learns (e.g., is trained to determine) appropriate weight values to achieve a desired output for a given input during a training, or learning, stage. Before the neural net is trained, each weight may be individually assigned an initial (e.g., random and optionally non-zero) value, e.g. a random-number seed. Various methods of assigning initial weights are known in the art. The weights are then trained (optimized) so that for a given training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input or training input image/sample) is fed forward through the neural network to determine its actual output (e.g., vector output). An error for each output neuron, or output node, is then calculated based on the actual neuron output and a target training output for that neuron (e.g., a training output image/sample corresponding to the present training input image/sample). One then propagates back through the neural network (in a direction from the output layer back to the input layer) updating the weights based on how much effect each weight has on the overall error so that the output of the neural network moves closer to the desired training output. This cycle is then repeated until the actual output of the neural network is within an acceptable error range of the desired training output for the given training input. As it would be understood, each training input may require many back-propagation iterations before achieving a desired error range. Typically an epoch refers to one back-propagation iteration (e.g., one forward pass and one backward pass) of all the training samples, such that training a neural network may require many epochs. Generally, the larger the training set, the better the performance of the trained ML model, so various data augmentation methods may be used to increase the size of the training set. For example, when the training set includes pairs of corresponding training input images and training output images, the training images may be divided into multiple corresponding image segments (or patches). Corresponding patches from a training input image and training output image may be paired to define multiple training patch pairs from one input/output image pair, which enlarges the training set. Training on large training sets, however, places high demands on computing resources, e.g. memory and data processing resources. Computing demands may be reduced by dividing a large training set into multiple mini-batches, where the mini-batch size defines the number of training samples in one forward/backward pass. In this case, and one epoch may include multiple mini-batches. Another issue is the possibility of a NN overfitting a training set such that its capacity to generalize from a specific input to a different input is reduced. Issues of overfitting may be mitigated by creating an ensemble of neural networks or by randomly dropping out nodes within a neural network during training, which effectively removes the dropped nodes from the neural network. Various dropout regulation methods, such as inverse dropout, are known in the art.

It is noted that the operation of a trained NN machine model is not a straight-forward algorithm of operational/analyzing steps. Indeed, when a trained NN machine model receives an input, the input is not analyzed in the traditional sense. Rather, irrespective of the subject or nature of the input (e.g., a vector defining a live image/scan or a vector defining some other entity, such as a demographic description or a record of activity) the input will be subjected to the same predefined architectural construct of the trained neural network (e.g., the same nodal/layer arrangement, trained weight and bias values, predefined convolution/deconvolution operations, activation functions, pooling operations, etc.), and it may not be clear how the trained network's architectural construct produces its output. Furthermore, the values of the trained weights and biases are not deterministic and depend upon many factors, such as the amount of time the neural network is given for training (e.g., the number of epochs in training), the random starting values of the weights before training starts, the computer architecture of the machine on which the NN is trained, selection of training samples, distribution of the training samples among multiple mini-batches, choice of activation function(s), choice of error function(s) that modify the weights, and even if training is interrupted on one machine (e.g., having a first computer architecture) and completed on another machine (e.g., having a different computer architecture). The point is that the reasons why a trained ML model reaches certain outputs is not clear, and much research is currently ongoing to attempt to determine the factors on which a ML model bases its outputs. Therefore, the processing of a neural network on live data cannot be reduced to a simple algorithm of steps. Rather, its operation is dependent upon its training architecture, training sample sets, training sequence, and various circumstances in the training of the ML model.

In summary, construction of a NN machine learning model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node-interconnections in the neural network are incrementally adjusted in order to reduce an error between an actual output of the neural network and the desired training output. In this manner, a multi-layer feedforward neural network (such as discussed above) may be made capable of approximating any measurable function to any desired degree of accuracy. The result of the learning stage is a (neural network) machine learning (ML) model that has been learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 15 and 16, convolutional neural networks (CNN) are also made up of neurons that have learnable weights and biases. Each neuron receives inputs, performs an operation (e.g., dot product), and is optionally followed by a non-linearity. The CNN, however, may receive raw image pixels at one end (e.g., the input end) and provide classification (or class) scores at the other end (e.g., the output end). Because CNNs expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of all of the neurons in a fully-connected NN. The final output layer of a CNN may reduce a full image into a single vector (classification) arranged along the depth dimension.

Figure 18:
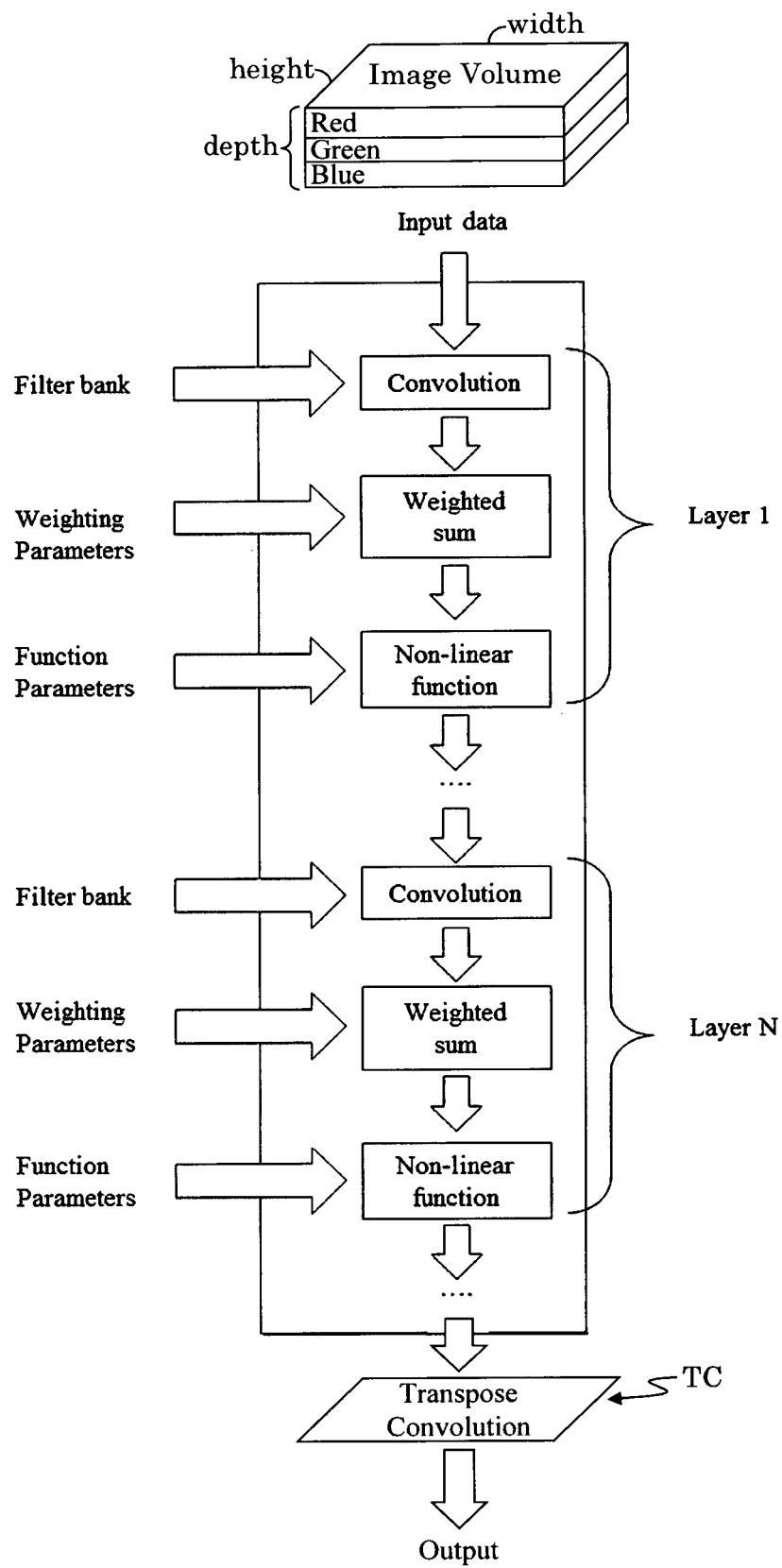
FIG. 18 illustrates an example convolutional neural network architecture.

FIG. 18 provides an example convolutional neural network architecture. A convolutional neural network may be defined as a sequence of two or more layers (e.g., Layer 1 to Layer N), where a layer may include a (image) convolution step, a weighted sum (of results) step, and a non-linear function step. The convolution may be performed on its input data by applying a filter (or kernel), e.g. on a moving window across the input data, to produce a feature map. Each layer and component of a layer may have different pre-determined filters (from a filter bank), weights (or weighting parameters), and/or function parameters. In the present example, the input data is an image, which may be raw pixel values of the image, of a given pixel height and width. In the present example, the input image is illustrated as having a depth of three color channels RGB (Red, Green, and Blue). Optionally, the input image may undergo various preprocessing, and the preprocessing results may be input in place of, or in addition to, the raw input image. Some examples of image preprocessing may include: retina blood vessel map segmentation, color space conversion, adaptive histogram equalization, connected components generation, etc. Within a layer, a dot product may be computed between the given weights and a small region they are connected to in the input volume. Many ways of configuring a CNN are known in the art, but as an example, a layer may be configured to apply an elementwise activation function, such as max (0,x) thresholding at zero. A pooling function may be performed (e.g., along the x-y directions) to down-sample a volume. A fully-connected layer may be used to determine the classification output and produce a one-dimensional output vector, which has been found useful for image recognition and classification. However, for image segmentation, the CNN would need to classify each pixel. Since each CNN layers tends to reduce the resolution of the input image, another stage is needed to up-sample the image back to its original resolution. This may be achieved by application of a transpose convolution (or deconvolution) stage TC, which typically does not use any predefine interpolation method, and instead has learnable parameters.

Convolutional Neural Networks have been successfully applied to many computer vision problems. As explained above, training a CNN generally requires a large training dataset. The U-Net architecture is based on CNNs and can generally can be trained on a smaller training dataset than conventional CNNs.

Figure 19:
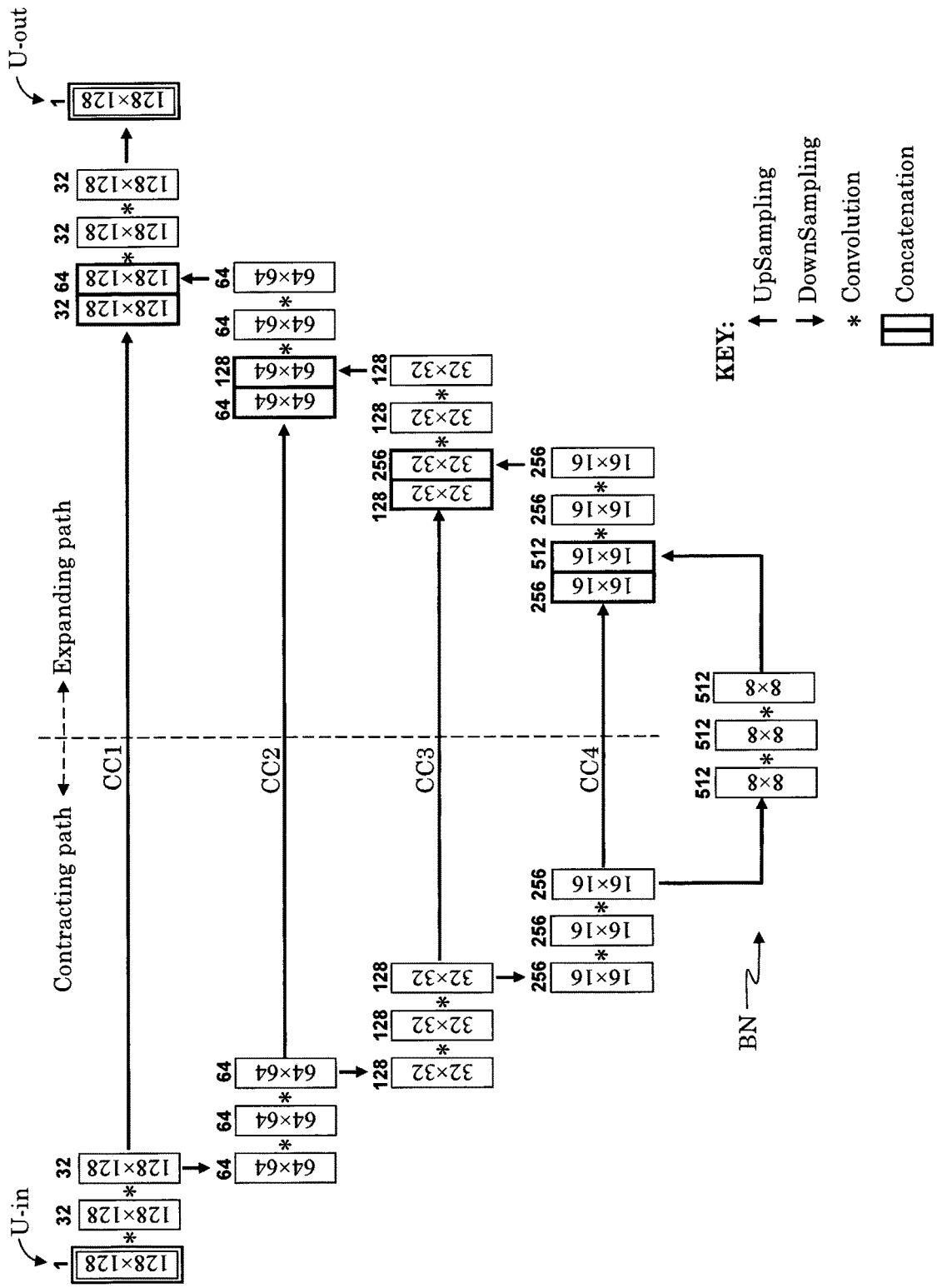
FIG. 19 illustrates an example U-Net architecture.

FIG. 19 illustrates an example U-Net architecture. The present exemplary U-Net includes an input module (or input layer or stage) that receives an input U-in (e.g., input image or image patch) of any given size (e.g., 128 by 128 pixels in size). The input image may be a fundus image, an OCT/OCTA en face, B-scan image, etc. It is to be understood, however, that the input may be of any size and dimension. For example, the input image may be an RGB color image, monochrome image, volume image, etc. The input image undergoes a series of processing layers, each of which is illustrated with exemplary sizes, but these sizes are illustration purposes only and would depend, for example, upon the size of the image, convolution filter, and/or pooling stages. The present architecture consists of a contracting path (comprised of four encoding modules) followed by an expanding path (comprised of four decoding modules), and four copy-and-crop links (e.g., CC1 to CC4) between corresponding modules/stages that copy the output of one encoding modules in the contracting path and concatenates it to the input of a correspond decoding module in the expanding path. This results in a characteristic U-shape, from which the architecture draws its name. The contracting path is similar to an encoder, and its basic function is to capture context via compact feature maps. In the present example, each encoding modules in the contracting path includes two convolutional neural network layers, which may be followed by one max pooling layer (e.g., Down-Sampling layer). For example, input image U_in undergoes two convolution layers, each with 32 feature maps. The number of feature maps may double at each pooling, starting with 32 feature maps in the first block, 64 in the second, and so on. The contracting path thus forms a convolutional network consisting of a plurality of encoding modules (or stages), each providing a convolution stage, followed by an activation function (e.g., a rectified linear unit, ReLU or sigmoid layer) and a max pooling operation. The expanding path is similar to a decoder, and its function is to provide localization and to retain spatial information despite the down sampling and any max-pooling performed in the contracting stage. In the contracting path, spatial information is reduced while feature information is increased. The expanding path includes a plurality of decoding modules, where each decoding module concatenates its current value with the output of a corresponding encoding module. That is, the feature and spatial information are combined in the expanding path through a sequence of up-convolutions (e.g., UpSampling or transpose convolutions or deconvolutions) and concatenations with high-resolution features from the contracting path (e.g., via CC1 to CC4). Thus, the output of a deconvolution layer is concatenated with the corresponding (optionally cropped) feature map from the contracting path, followed by two convolutional layers and activation function (with optional batch normalization). The output from the last module in the expanding path may be fed to another processing/training block or layer, such as a classifier block, that may be trained along with the U-Net architecture.

The module/stage (BN) between the contracting path and the expanding path may be termed the "bottleneck." The bottleneck BN may consist of two convolutional layers (with batch normalization and optional dropout).

Computing Device/System

Figure 20:
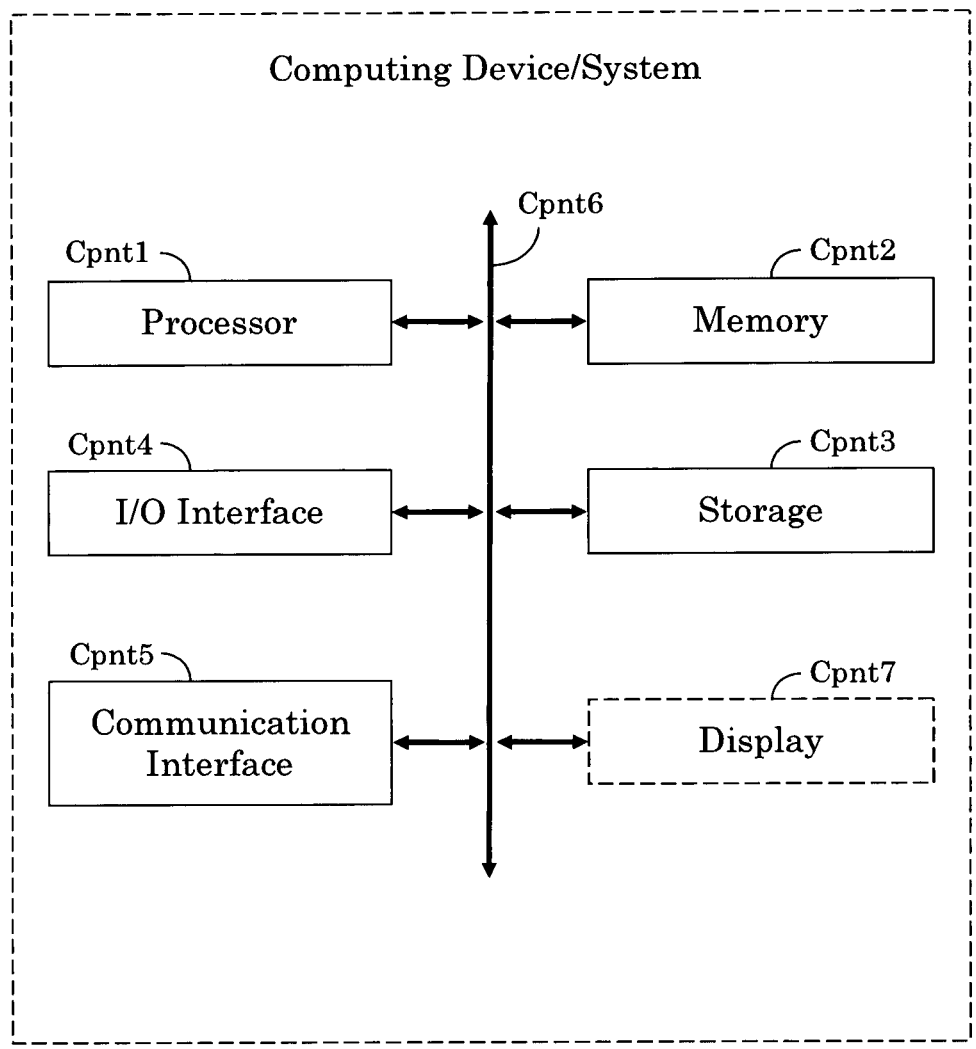
FIG. 20 illustrates an example computer system (or computing device or computer device).

FIG. 20 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to computer system, and include one or more of a disk drive (e.g., hard disk drive, HDD, or solid state drive, SSD), flash memory, ROM, EPROM, optical disc, a magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method for classifying geographic atrophy (GA) in an eye, comprising:
   acquiring, using an ophthalmic diagnostic device, an image of the fundus of the eye;
   submitting, using a computer processor, the acquired image to an automated GA region identification process including a phenotype classifier that is based on a machine learning model, wherein the phenotype classifier identifies GA regions, and then classifies the identified GA regions as a banded phenotype or a diffused phenotype; and
   displaying, using the computer processor, the result of the phenotype classifier on an electronic display or storing the result for further processing;
   wherein the automated GA region identification process is a two-stage GA region identification process, including a first stage based on a supervised pixel classifier that applies a pixel-by-pixel classification to the acquired image to identify first GA regions, and a second stage that uses the first GA regions as starting points in an active contour segmentation process that defines second GA regions, the defined second GA regions being identified as banded phenotype or diffused phenotype.

2. The method of claim 1, wherein the phenotype classifier is a neural network trained using a training output set of eye fundus images with manually delineated GA regions with their phenotypes identified, and using a training input set of the same eye fundus images without the delineated GA regions and without the identified phenotypes; and wherein retinal vessels are removed from the fundus images in the training input set and the training output set prior to training the neural network.

3. The method of claim 1, further comprising: determining a region of interest (ROI) within the acquired image, the ROI including the macula of the eye; wherein the phenotype classifier limits the processing to the ROI.

4. The method of claim 1, further comprising: determining an image quality (IQ) measure of the acquired image; wherein the acquired image is submitted to the phenotype classifier in response to the determined image quality measured being higher than a predefined IQ threshold.

5. The method of claim 1, wherein the supervised pixel classifier is one of a trained neural network or a support vector machine.

6. The method of claim 1, wherein the active contour segmentation process applies Chan-Vese active contour segmentation.

7. The method of claim 1, wherein phenotype classification is based on the junctional zones of the identified GA regions.

8. The method of claim 1, wherein retinal vessels are removed from the acquired image prior to identifying GA regions.

9. A method for classifying geographic atrophy (GA) in an eye, comprising:
   acquiring, using an ophthalmic diagnostic device, an image of the fundus of the eye;
   submitting, using a computer processor, the acquired image to a phenotype classifier that is based on a machine learning model, wherein the phenotype classifier identifies GA regions, and then classifies the identified GA regions as a banded phenotype or a diffused phenotype; and
   displaying, using the computer processor, the result of the phenotype classifier on an electronic display or storing the result for further processing,
   wherein for each identified GA region:
      the phenotype classifier maps a currently identified GA region to a 3D space and determines the surface area of the 3D mapped GA region; and
      in response to surface area of the 3D mapped GA region being smaller than a predefined minimum area threshold, reclassifying the currently identified GA region as a non-GA region.

10. A method for classifying geographic atrophy (GA) in an eye, comprising:
   acquiring, using an ophthalmic diagnostic device, an image of the fundus of the eye;
   submitting, using a computer processor, the acquired image to a phenotype classifier that is based on a machine learning model, wherein the phenotype classifier identifies GA regions, and then classifies the identified GA regions as a banded phenotype or a diffused phenotype; and
   displaying, using the computer processor, the result of the phenotype classifier on an electronic display or storing the result for further processing,
   wherein for each identified GA region, the phenotype classifier:
      determines a first measure, the first measure being one of a contour-non-uniformity measure or intensity-uniformity measure in a vicinity adjacent to, and along, the perimeter of a currently identified GA region; and in response to the determined first measure being higher than a first threshold, classifies the currently identified GA region as high-progression-rate GA.

11. The method of claim 10, wherein the phenotype classifier: in response to the first measure not being higher than the first threshold, determines a second measure, the second measure being the other of the contour-non-uniformity measure or intensity-uniformity measure; and in response to the second measure being higher than a second threshold, classifies the currently identified GA region as high-progression-rate GA.

12. A method for classifying geographic atrophy (GA) in an eye, comprising:
   acquiring, using an ophthalmic diagnostic device, an image of the fundus of the eye;
   submitting, using a computer processor, the acquired image to a phenotype classifier that is based on a machine learning model, wherein the phenotype classifier identifies GA regions, and then classifies the identified GA regions as a banded phenotype or a diffused phenotype; and
   displaying, using the computer processor, the result of the phenotype classifier on an electronic display or storing the result for further processing,
   wherein for a currently identified GA region, the phenotype classifier:
      determines a contour-non-uniformity measure in a vicinity adjacent to, and along, the perimeter of the currently identified GA region; and
      in response to the determined contour-non-uniformity measure being greater than a predefined non-uniformity threshold, classifies the currently identified GA region as 'diffused' phenotype.

13. The method of claim 12, wherein the non-uniformity threshold is based on a standardized mean contour variation of a library of sample GA regions.

14. A method for classifying geographic atrophy (GA) in an eye, comprising:
   acquiring, using an ophthalmic diagnostic device, an image of the fundus of the eye;
   submitting, using a computer processor, the acquired image to a phenotype classifier that is based on a machine learning model, wherein the phenotype classifier identifies GA regions, and then classifies the identified GA regions as a banded phenotype or a diffused phenotype; and
   displaying, using the computer processor, the result of the phenotype classifier on an electronic display or storing the result for further processing,
   wherein for a currently identified GA region, the phenotype classifier:
      determines an intensity-uniformity measure in a vicinity adjacent to, and along, the perimeter of the currently identified GA region; and
      in response to the determined intensity-uniformity measure being greater than a predefined intensity-uniformity threshold, classifies the currently identified GA region as 'banded' phenotype.

15. The method of claim 14, wherein: determining the intensity-uniformity measure includes selecting a set of random points along the perimeter of the currently identified GA region and determining ridges and valleys of pixel intensities along directions normal to the contour of the perimeter extending from the random points; and the intensity-uniformity threshold is based on a standardize mean of ridges and values of pixel intensities along the junctional zones of sample GA regions.

16. A system for classifying geographic atrophy (GA) in an eye, comprising:
   an ophthalmic diagnostic device configured to acquire an image of the fundus of the eye;
   a computer processor configured to submit the acquired image to an automated GA region identification process including a phenotype classifier that is based on a machine learning model, wherein the phenotype classifier identifies GA regions;
   the computer processor further configured to classify the identified GA regions as a banded phenotype or a diffused phenotype; and
   the computer processor further configured to display the result of the phenotype classifier on an electronic display or storing the result for further processing,
   wherein the automated GA region identification process is a two-stage GA region identification process, including a first stage based on a supervised pixel classifier that applies a pixel-by-pixel classification to the acquired image to identify first GA regions, and a second stage that uses the first GA regions as starting points in an active contour segmentation process that defines second GA regions, the defined second GA regions being identified as banded phenotype or diffused phenotype.

* * * * *